US008177810B2

(12) United States Patent
Ferree

(10) Patent No.: US 8,177,810 B2
(45) Date of Patent: *May 15, 2012

(54) METHODS OF ANNULUS AND LIGAMENT RECONSTRUCTION USING FLEXIBLE DEVICES

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 831 days.

This patent is subject to a terminal disclaimer.

(21) Appl. No.: 12/173,775

(22) Filed: Jul. 15, 2008

(65) Prior Publication Data

US 2009/0024165 A1    Jan. 22, 2009

Related U.S. Application Data

(60) Provisional application No. 60/961,004, filed on Jul. 17, 2007.

(51) Int. Cl.
*A61B 17/70* (2006.01)
*A61B 17/04* (2006.01)
*A61B 19/00* (2006.01)

(52) U.S. Cl. ........ 606/246; 606/254; 606/264; 606/301; 128/898

(58) Field of Classification Search ................... 606/246, 606/264, 254, 300, 301, 263, 279, 151, 103, 606/74, 59, 257, 255, 228, 233, 232; 128/898
See application file for complete search history.

(56) References Cited

U.S. PATENT DOCUMENTS

| | | | | |
|---|---|---|---|---|
| 5,681,310 A * | 10/1997 | Yuan et al. | .................... | 606/281 |
| 6,248,106 B1 | 6/2001 | Ferree | | |
| 6,296,643 B1 * | 10/2001 | Hopf et al. | .................... | 606/263 |
| 6,423,065 B2 | 7/2002 | Ferree | | |
| 6,626,909 B2 * | 9/2003 | Chin | .............................. | 606/276 |
| 6,645,211 B2 * | 11/2003 | Magana | ........................ | 606/247 |
| 6,878,167 B2 | 4/2005 | Ferree | | |
| 7,201,774 B2 | 4/2007 | Ferree | | |
| 7,338,531 B2 * | 3/2008 | Ellis et al. | .................. | 623/23.74 |

* cited by examiner

*Primary Examiner* — Pedro Philogene
(74) *Attorney, Agent, or Firm* — Pandiscio & Pandiscio

(57) ABSTRACT

Methods for providing a flexible spinal stabilization system operative to prevent lateral bending, extension, and rotation across two or more adjacent vertebrae are described. Broadly, the invention utilizes a pair of connectors on each vertebrae, and flexible elongated elements, such as sutures or cables, in an axial and crisscrossed pattern to provide an arrangement that resists extension, lateral bending, and torsional/rotational motion. In some embodiments, the flexible stabilization system includes a pair of locking anchors and a pair of hook-like anchors. The locking anchors are pre-threaded with a suture in a loose looped configuration before insertion into the vertebra. Once the locking anchors have been inserted, the suture loops can be looped over hook-like anchors inserted into an adjacent vertebrae to join the vertebrae and apply tension across the disc space. In some embodiments, the hook-like anchors can have multiple hooks for use in joining multiple vertebral levels.

26 Claims, 30 Drawing Sheets

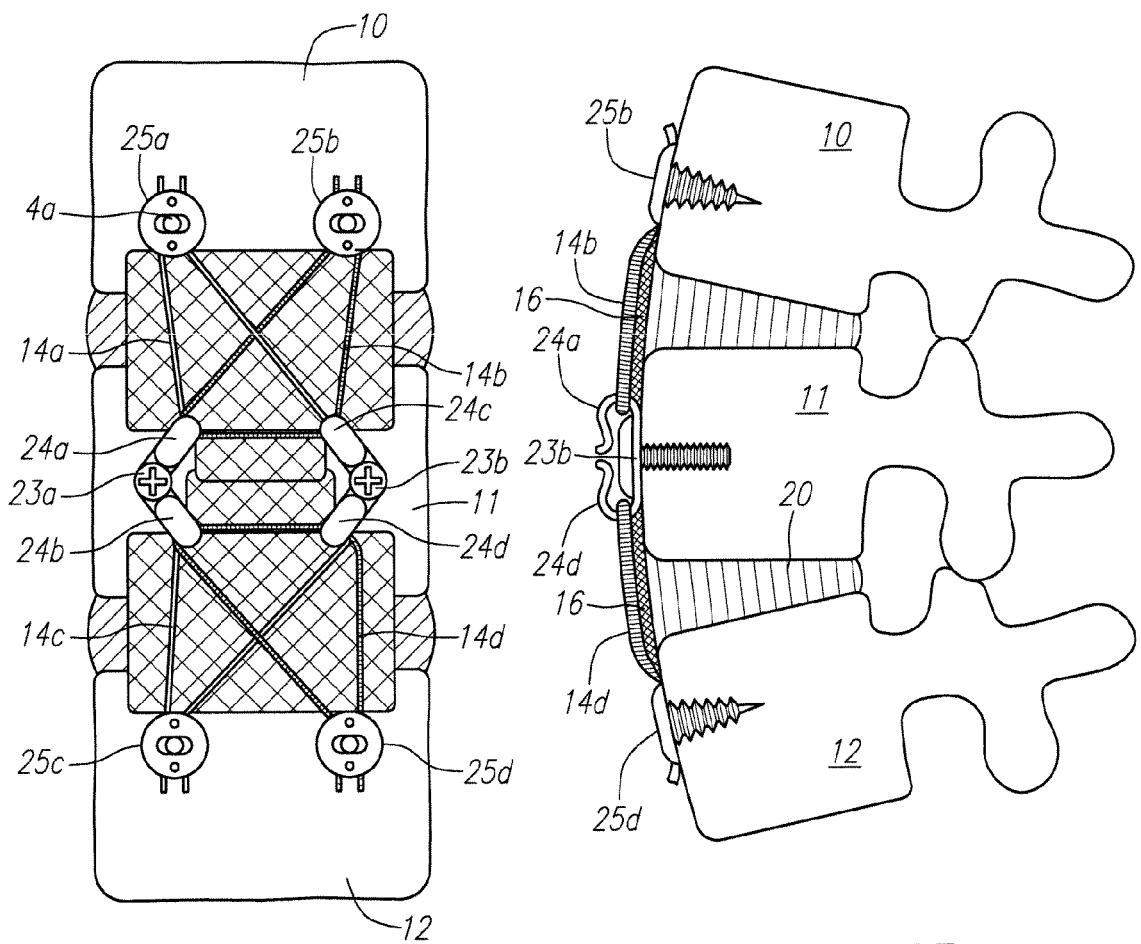
FIG. 2A
FIG. 2B
FIG. 2C
FIG. 2D

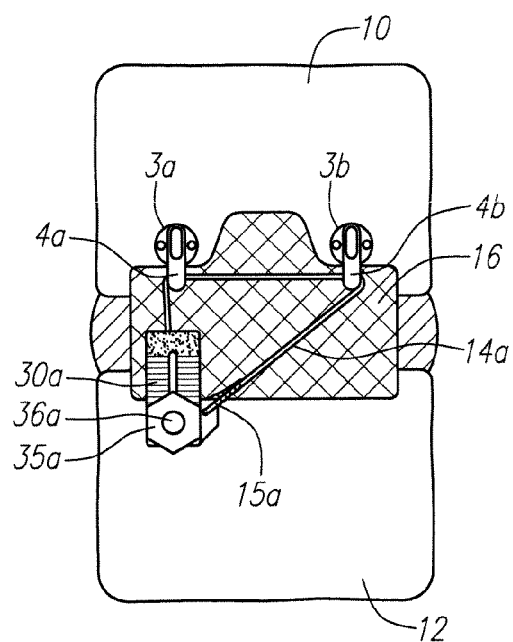
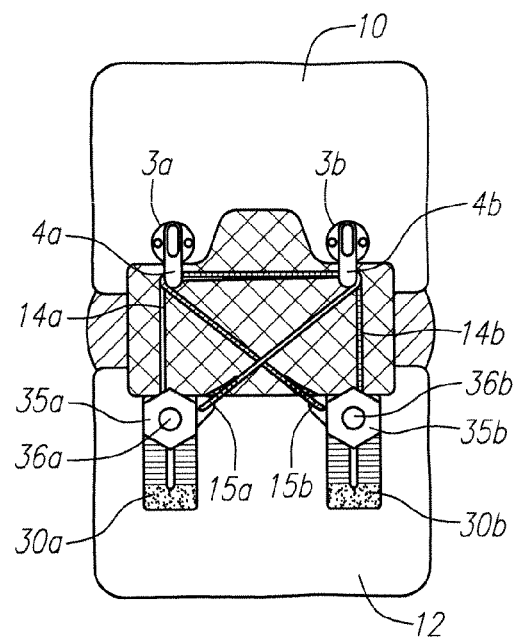
FIG. 7A
FIG. 7B
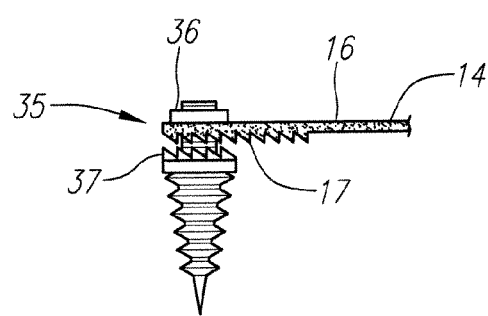
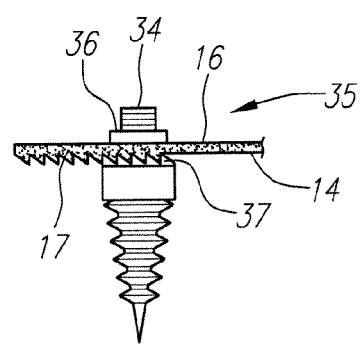
FIG. 7C
FIG. 7D

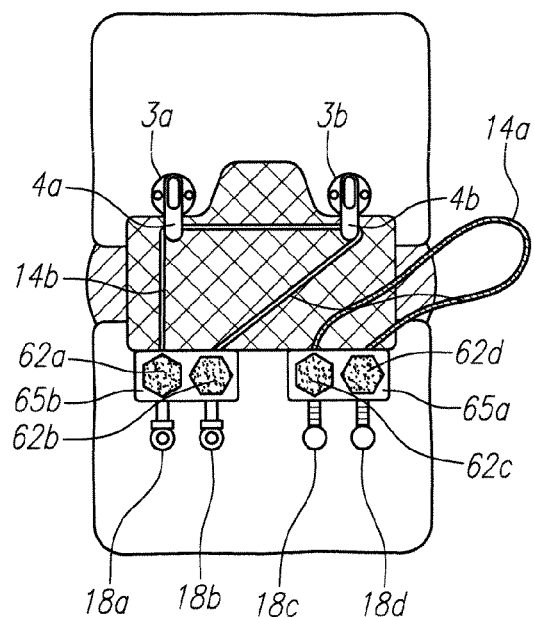
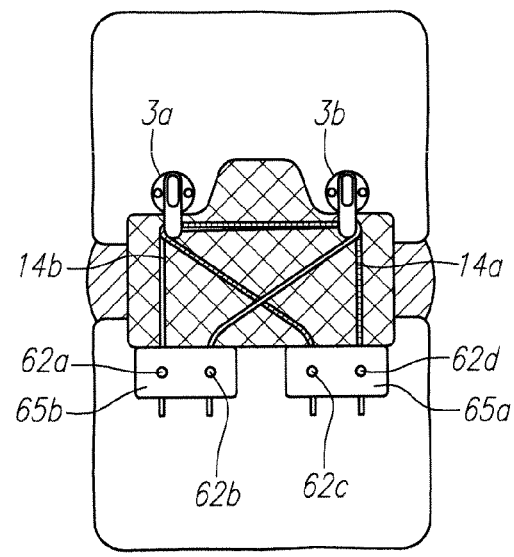
FIG. 8A  FIG. 8B
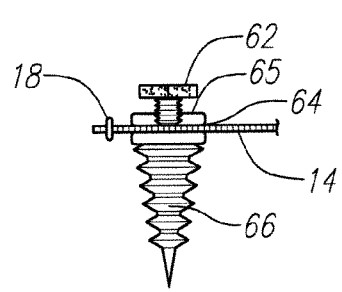
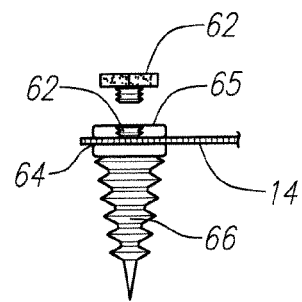
FIG. 8C  FIG. 8D

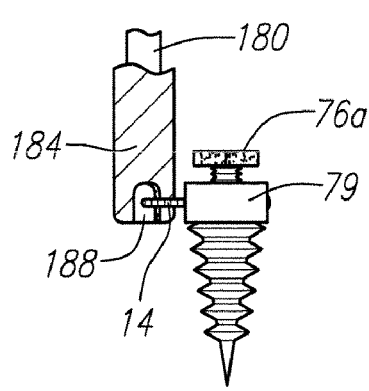
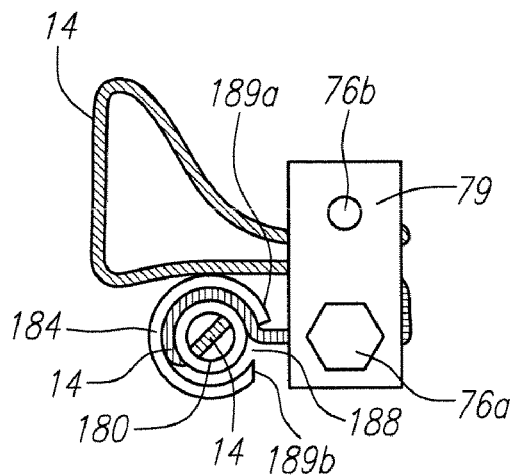
FIG. 16A              FIG. 16B
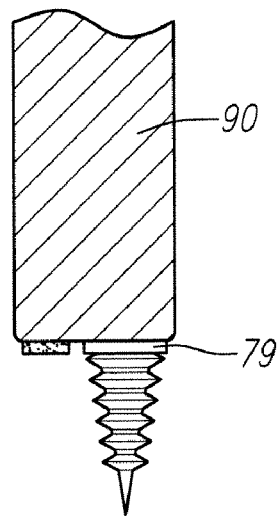
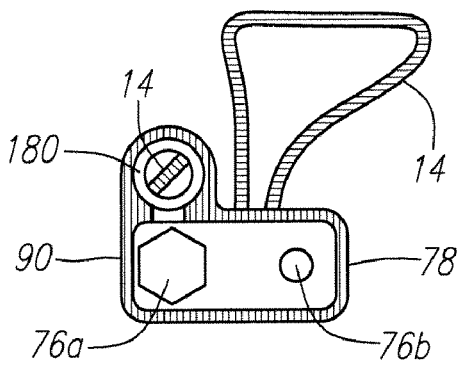
FIG. 17A              FIG. 17B

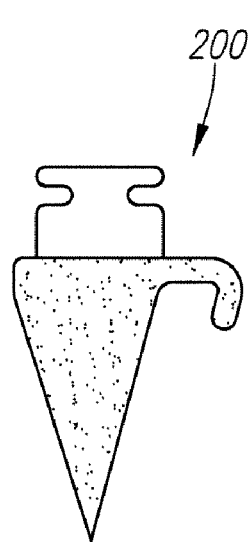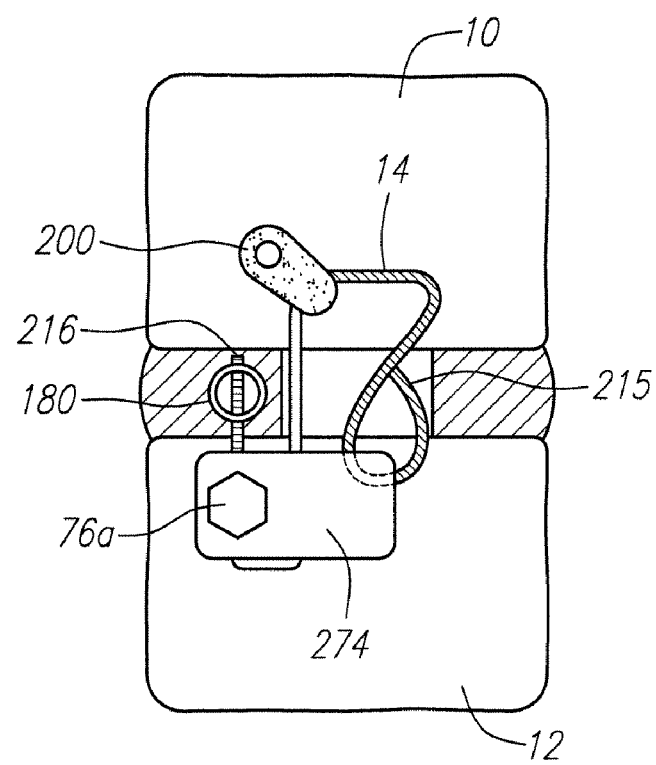
FIG. 20A                    FIG. 20B

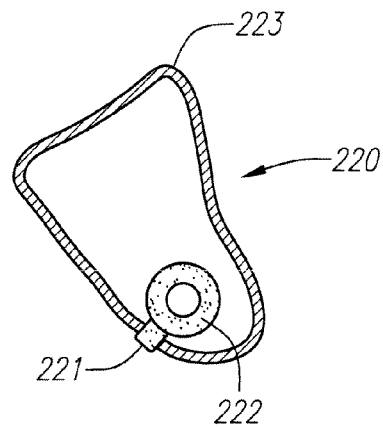
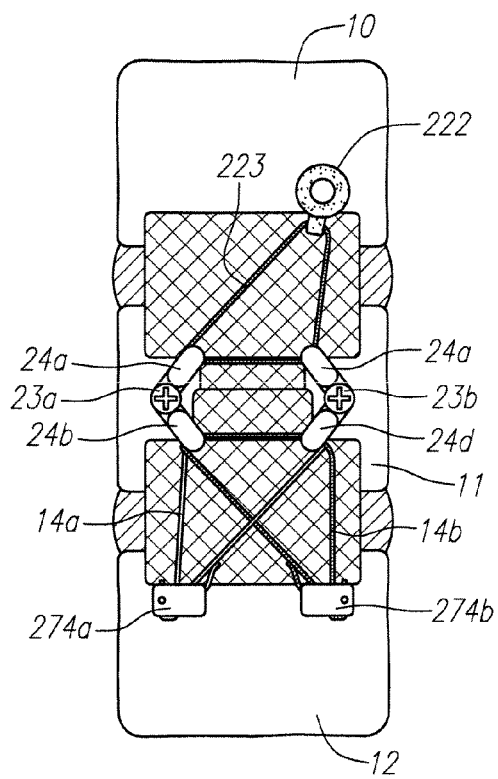
FIG. 21A
FIG. 21B
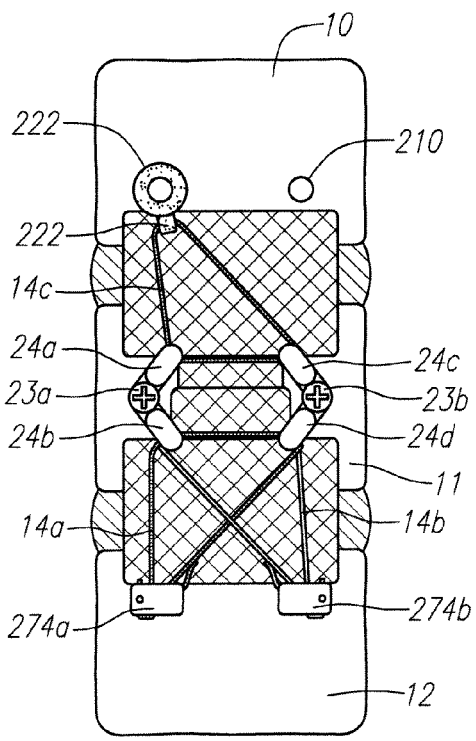
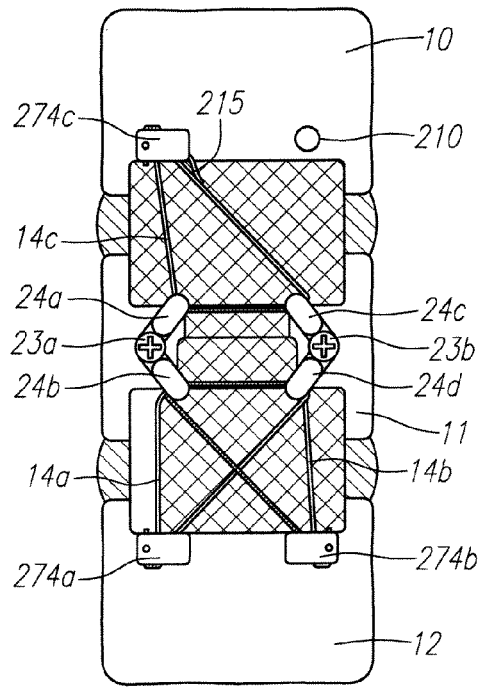
FIG. 21C
FIG. 21D

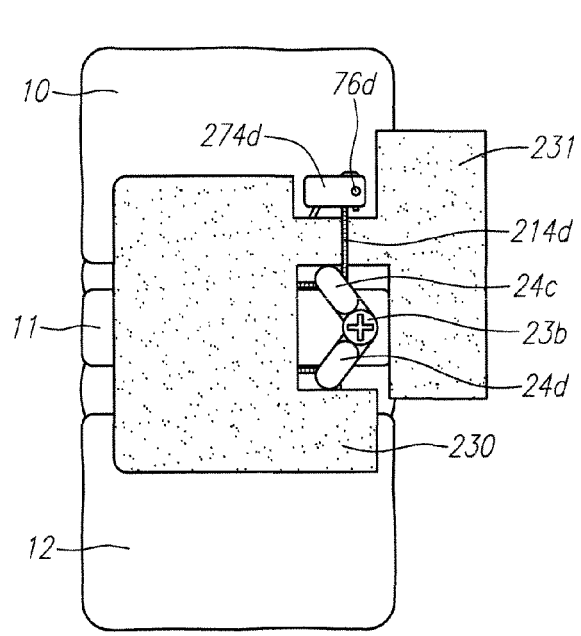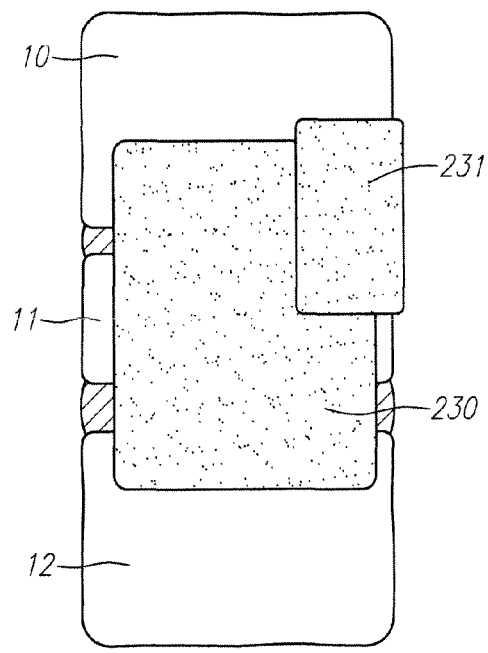
FIG. 21E              FIG. 21F
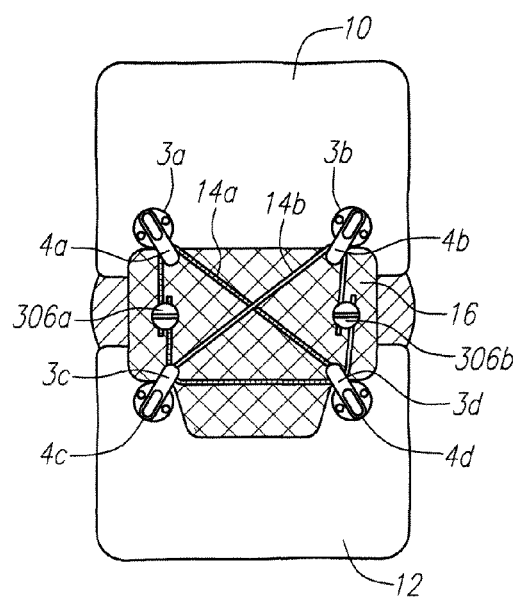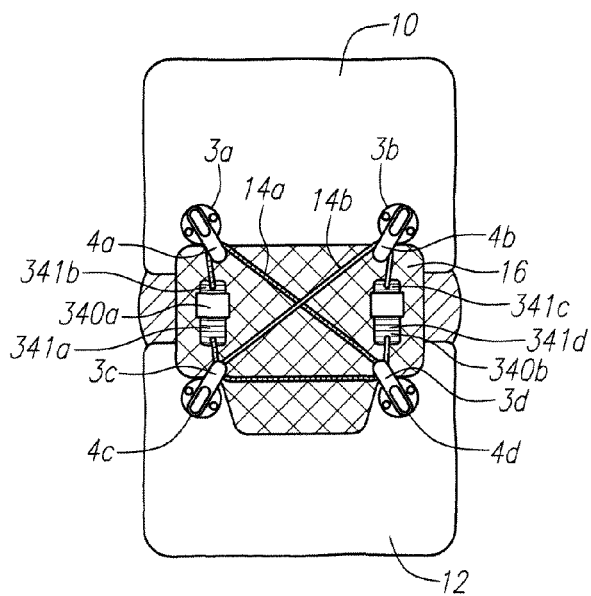
FIG. 22               FIG. 23

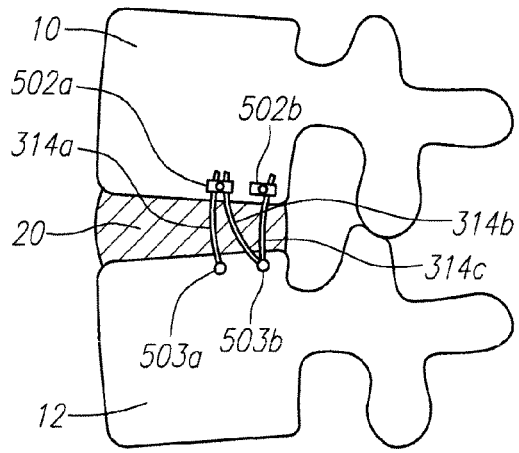
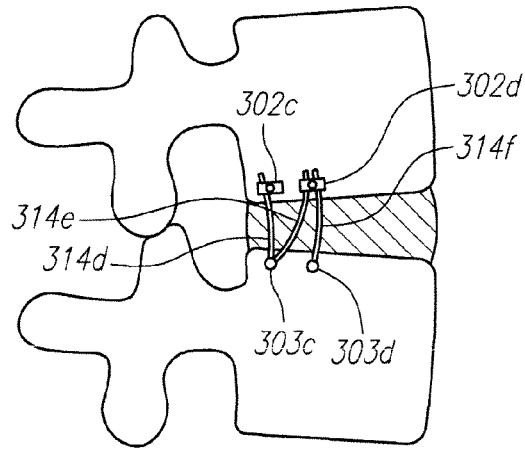
FIG. 32A      FIG. 32B
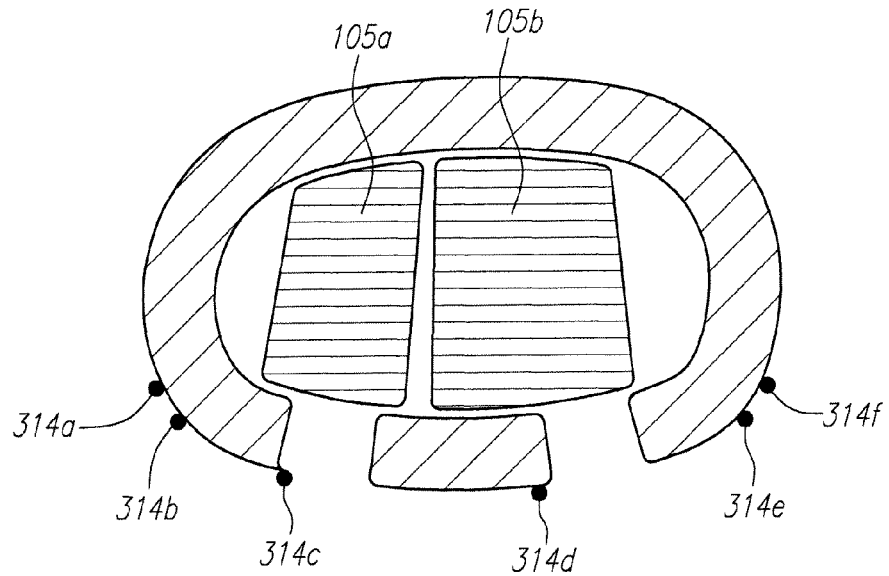
FIG. 32C
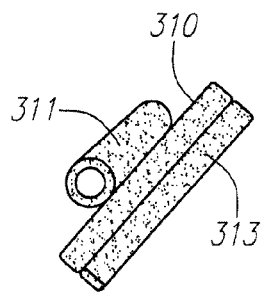
FIG. 33A

METHODS OF ANNULUS AND LIGAMENT RECONSTRUCTION USING FLEXIBLE DEVICES

RELATED APPLICATIONS

This application claims the benefit of U.S. Provisional Application 60/961,004, filed Jul. 17, 2007, entitled "Bone, Joint, and Ligament Reconstruction with Flexible Devices." This application is related to co-pending applications 60/808,795, filed May 26, 2006, entitled "Fastening Assemblies for Disc Herniation Repair and Methods of Use" and 60/861,499, filed Nov. 28, 2006, entitled "Anulus and Spinal Ligament Reconstruction" and 60/901,230, filed Feb. 13, 2007, entitled "Anulus and Ligament Reconstruction using Bands." The application is also related to U.S. Pat. Nos. 6,248,106 and 6,423,065. All of the above-referenced patent and applications are hereby expressly incorporated by reference in their entirety.

FIELD OF THE INVENTION

The subject invention resides in methods and apparatus for stabilizing a spinal segment using one or more fixation members attached to adjacent vertebrae. The invention is particularly well suited to the prevention of excessive spinal motion.

BACKGROUND

The human intervertebral disc is an oval to kidney bean-shaped structure of variable size depending on the location in the spine. The outer portion of the disc is known as the anulus fibrosus (AF). The anulus fibrosus is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the anulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and anulus functions are compromised. The nucleus becomes thinner and less able to handle compression loads. The anulus fibers become redundant as the nucleus shrinks. The redundant annular fibers are less effective in controlling vertebral motion. This disc pathology can result in: 1) bulging of the anulus into the spinal cord or nerves; 2) narrowing of the space between the vertebra where the nerves exit; 3) tears of the anulus as abnormal loads are transmitted to the anulus and the anulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either removes the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in co-pending U.S. patent application Ser. No. 10/407,554 and U.S. Pat. No. 6,878,167, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often applies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

SUMMARY

A portion of the anulus fibrosus and a portion of the ligaments of the spine are excised to allow insertion of materials and devices into the disc space. For example, a portion of the anterior half of the anulus fibrosus and a portion of the anterior longitudinal ligament (ALL) are excised to enable insertion of bone growth promoting materials and fusion devices in interbody fusion procedures. Removal of portions of the anulus fibrosus and anterior longitudinal ligament increase the flexibility of the spine and allow excessive motion of the spine. For example, removal of the tissues mentioned permits excessive spinal extension, lateral bending, and axial rotation. Destabilizing the spine decreases the chance of a successful fusion. The invention may be used to increase the stiffness of the operated segment of the spine. Increasing the stiffness of the spine facilitates spinal fusion.

A portion of the anulus fibrosus and a portion of the anterior longitudinal ligament are also excised to enable insertion of motion preserving devices into the disc. For example, Total Disc Replacements (TDRs) and Nucleus Replacements (NRs) are often inserted through the anterior portion of discs. Excessive spinal extension, lateral bending, and axial rotation following excision of the spinal tissues and insertion of motion preserving devices into the disc space places excessive force on the facets of the spine. Biomechanical studies show the forces across the facets at the operated level of the spine can be doubled by motion preserving devices and the techniques used to insert such devices. Excessive force on the facets may lead to degeneration of the facets. Degeneration of the facets may cause low back pain.

The invention may also be used to tether the spine. Tethering the immature spine enables correction of spinal deformities as the spine grows. The invention may incorporate materials that encourage the growth of connective tissue into components of the various devices taught in the invention. The invention may also incorporate materials that prevent the growth of connective tissue into components of the various devices taught in the invention. Preventing or limiting connective in-growth may be used to diminish adhesions at the surgical site.

The invention may also be used to treat other orthopaedic conditions. For example, the invention may be used to treat fractures, such as fractures of the patella and olecranon. The invention may also be used to immobilize joints during fusion procedures. The invention may also be used with prosthetic joint.

BRIEF DESCRIPTION OF THE DRAWINGS

FIG. 2A is an anterior view of the spine and an alternative embodiment of the invention.

FIG. 2B is a lateral view of a partial saggital cross-section of a portion of the spine and the embodiment of the invention drawn in FIG. 2A.

FIG. 2C is an anterior view of the hook-like anchors drawn in FIGS. 2A-B.

FIG. 2D is a lateral view of the anchor shown in FIG. 2C.

FIG. 7A is an anterior view of a portion of the spine and an alternative embodiment of the invention.

FIG. 7B is an anterior view of a portion of the spine and the embodiment illustrated in FIG. 7A.

FIG. 7C is a lateral view of the anchor and longitudinal fixation element illustrated in FIGS. 7A-B.

FIG. 7D is a lateral view of the anchor an longitudinal fixation element illustrated in FIG. 7C.

FIG. 8A is an anterior view of a portion of the spine and an alternative embodiment of the invention.

FIG. 8B is an anterior view of a portion of the spine and the embodiment illustrated in FIG. 8A.

FIG. 8C is a lateral view of the anchor and longitudinal fixation element illustrated in FIGS. 8A-B.

FIG. 8D is a lateral view of the anchor and longitudinal fixation element illustrated in FIGS. 8A-C.

FIG. 16A is a lateral view of an alternative embodiment of a cutting tool.

FIG. 16B is a cross-section of a tensioning tool and the cutting tool in FIG. 16A used on a longitudinal fixation element and an anchor of the present invention.

FIG. 17A is a lateral view of the anchor and tensioning tool in FIG. 15A being used with an anchor driver.

FIG. 17B is an axial cross-section of the tools in FIG. 17A being used on an anchor and longitudinal fixation element.

FIG. 20A is a lateral view of an anchor placement tool.

FIG. 20B is an anterior view of a portion of the spine illustrating use of the anchor placement tool shown in FIG. 20A.

FIG. 21A illustrates an alternative embodiment of an anchor locator tool.

FIG. 21B is an anterior view of a portion of the spine illustrating the anchor locator tool of FIG. 21A used to locate a hole for an anchor in the cranial vertebrae.

FIG. 21C is an anterior view of a portion of the spine illustrating the anchor locator tool of FIG. 21A used to locate a hole for a second anchor in the cranial vertebrae.

FIG. 21D is an anterior view of a portion of the spine illustrating an anchor placed in a hole in the cranial vertebrae made with the anchor locator tool shown in FIG. 21A.

FIG. 21E is an anterior view of the embodiment in FIG. 21D illustrating an anti-adhesion component placed over most of the flexible fixation system.

FIG. 21F is an anterior view of the embodiment in FIG. 21F illustrating a flap of the anti-adhesion component folded over the exposed anchors and flexible longitudinal fixation element.

FIG. 22 is an anterior view of a portion of the spine illustrating an alternative embodiment of a flexible fixation system using four hook anchors in the cranial and caudal vertebrae.

FIG. 23 is an anterior view of a portion of the spine illustrating an alternative embodiment of a flexible fixation system using four hook anchors in the cranial and caudal vertebrae.

FIG. 32A is a lateral view of a portion of the spine illustrating a flexible spinal stabilization system applied to the posterior-lateral portion of the spine.

FIG. 32B is a lateral view of the portion of the spine shown in FIG. 32A illustrating a flexible spinal stabilization system applied to the opposite posterior-lateral portion of the spine.

FIG. 32C is an axial cross-section of an intervertebral disc and the embodiments shown in FIGS. 32A-B.

FIG. 33A is an oblique view of an anti-adhesion sleeve that may be placed over the flexible longitudinal elements illustrated in FIGS. 32A-B

DETAILED DESCRIPTION

Figure 1A:
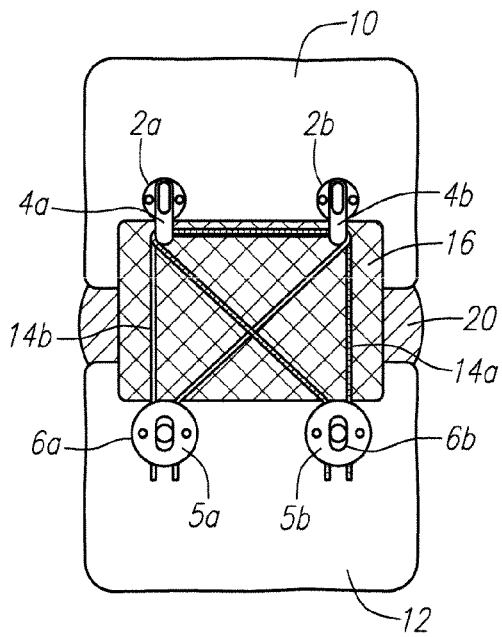
FIG. 1A is an anterior view of a portion of the spine and a flexible stabilization device.
Figure 1B:
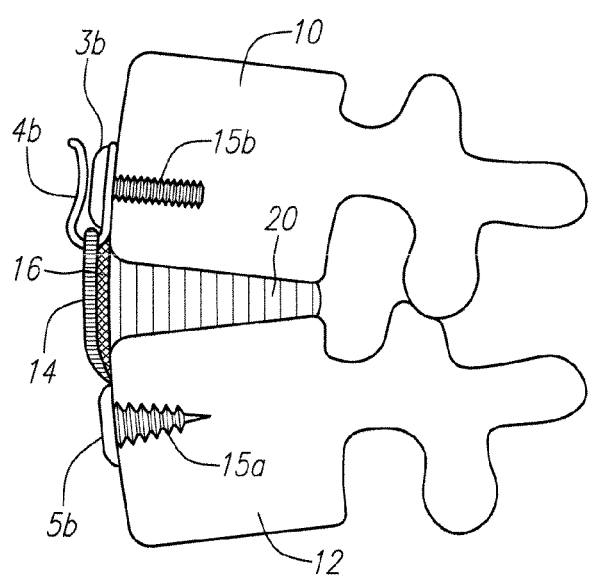
FIG. 1B is a lateral view of a partial saggital cross-section of a portion of the spine and the embodiment of the invention drawn in FIG. 1A.
Figure 1C:
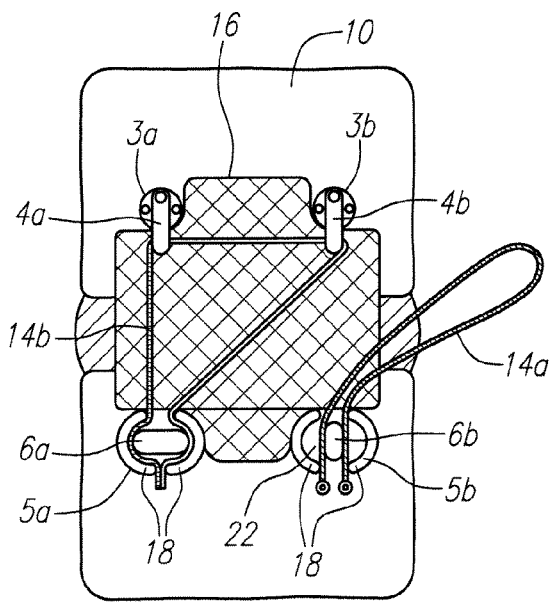
FIG. 1C is an anterior view of a portion of the spine and the embodiment of the invention drawn in FIG. 1A.

FIGS. 1A-1C illustrate a flexible stabilization system for minimizing and/or preventing lateral bending, extension and or rotation across adjacent vertebrae. Broadly, the invention utilizes a pair of connectors on each vertebrae, and flexible elongated elements, such as sutures or cables, in an axial and crisscrossed pattern to provide an arrangement that resists extension, lateral bending, and torsional/rotational motion. The invention may be used on the cervical, thoracic, lumbar, or sacral regions of the spine.

In one embodiment, as illustrated in FIG. 1A, the flexible stabilization system uses four anchors 3a,b and 5a,b and two flexible longitudinal fixation elements, or elongate elements, 14a,b to join upper and lower vertebrae 10 and 12, though the invention is applicable to multiple levels, as described elsewhere herein. Two hook anchors 3a,b were placed into cranial vertebra 10 that contain a first portion adapted for insertion into the vertebra 10 and a second portion having a hook 4a,b for capturing and holding the elongate elements 14a,b. Two cam operated anchors 5a,b, such as the cam-operated anchors described in U.S. Pat. No. 6,423,065 entitled "Cross-coupled vertebral stabilizers including cam-operated cable connectors," hereby incorporated by reference in its entirely for description of suitable cam anchors, were placed into caudal vertebra 12. Cam-operated anchors 5a,b include a first portion adapted for insertion into the vertebra 12 and a second portion for holding the elongate elements 14a,b under tension. The second, or holding portion, has a generally oblong member 6a,b, a pair of generally arcuate sleeves 18, and an annulus 22 disposed therebetween. As shown in more detail in FIG. 1C, the annulus 22 is adapted to receive first and second end regions of one of the first or second elongate elements 14a,b there through and extends along an axis perpendicular to a longitudinal axis of the first portion of each of the cam anchors 5a,b, i.e., extends along an axis generally perpendicular to the threaded portion inserted into the vertebrae 12. In use, a first flexible longitudinal fixation element 14a, such as a multifilament polyester suture, connects cam-operated anchor 5b to two hook-like anchors 3a,b. A second flexible longitudinal fixation element 14b connects cam-operated anchor 5a to two hook-like anchors 3a,b such that the flexible longitudinal elements form a cross-braced arrangement over the disc space between the vertebrae 10,12. Non-absorbable suture material, such as Orthocord (DePuy, Raynham Mass.), Fiberwire (Arthrex, Naples Fla.), or other such suture may be used for the flexible longitudinal fixation elements. The sutures are preferably size #2 to #5. Alternatively, the sutures could be size #1, 0, 00, or smaller. Alternatively, the sutures may be larger than #5. Other flexible materials, such as titanium cables, braided polyethylene, braided nylon, or other materials could be used for the flexible longitudinal fixation elements. The materials preferably have a diameter between about 0.5 mm and about 2.0 mm. Alternatively, the flexible longitudinal fixation elements could have diameters of about 0.1, 0.2, 0.3, 0.4, 2.1, 2.2, 2.3, or 2.4 mm or larger.

In some embodiments, the cam anchors 5a,b are be threaded with the flexible longitudinal fixation elements 14a,b prior to insertion in the spine such that the surgeon does not have to thread the longitudinal fixation elements 14a,b through the cam anchors 5a,b after the cam anchors 5a,b have been inserted into vertebrae 12. The longitudinal fixation elements 14a,b are pre-threaded through the annulus 22 of the cam anchors 5a,b in a loose configuration such that there is enough slack to easily place the loops of the longitudinal fixation elements 14a,b around the hooks 4a,b on anchors 3a,b in cranial vertebrae 10.

FIG. 1B is a lateral view of a partial sagittal cross section of a portion of the spine and the flexible stabilization device drawn in FIG. 1A. The shafts 15a,b of the cam operated anchors 5a,b are preferably about 4 to 7 mm in diameter. Alternatively, the shafts 15a,b of the cam-operated anchors 5a,b could be about 2, 3, 8, 9, or 10 mm in diameter or larger. The cam-operated anchors 5a,b are preferably about 12 to 35 mm long. Alternatively, the cam-operated anchors 5a,b could be about 6, 7, 8, 9, 10, 11, 36, 37, 38, 39, or 40 mm long or longer.

Figure 1D:
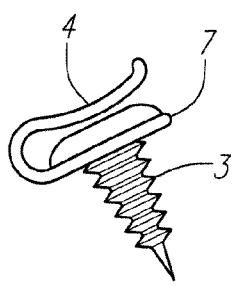
FIG. 1D is a lateral view of the hook-like anchors drawn in FIGS. 1A-C.

FIG. 1D is a lateral view of an embodiment of hook-like anchors for use with the flexible stabilization system illustrated in FIGS. 1A-1C. The anchors are preferably sized similar to the cam operated anchors. Hook-like washer 7 is located just below the head of the anchor. The shape of the washer 7 facilitates placement of the flexible longitudinal fixation element between the hook 4 of the washer 7 and the head of the anchor. The shape also facilitates retention of the flexible longitudinal fixation element within the hook 4 of the washer 7. The enlarged opening at the base of the washer 7 enables the flexible longitudinal fixation elements to slide through the hook-like washer. The washer is preferably about 3 to about 6 mm long, about 1 to about 4 mm wide, and about 1 to about 3 mm tall. Alternatively the washer could be about 2, about 7, or about 8 mm long or longer; about 0.3, about 0.4, about 0.5, about 0.6, about 0.7, about 0.8, about 0.9, about 5, about 6, about 7, or about 8 mm wide or wider; and about 0.3, about 0.4, about 0.5, about 0.6, about 0.7, about 0.8, about 0.9, about 4, about 5, about 6, or about 7 mm tall or taller. The hook-like anchors 3a,b and cam operated anchors 5a,b are preferably made of titanium or other MRI compatible material. Alternatively, the anchors could be made of plastic such as Delron, or a bioresorbable such as polylactic acid (PLA), polyglycolic acid (PGA), poly (ortho esters), poly(glycolide-co-trimethylene carbonate), poly-L-lactide-co-6-caprolactone, polyanhydrides, poly-n-dioxanone, poly(PHB-hydroxyvaleric acid), or combinations thereof.

In use, as shown in FIG. 1C, hook-like anchors 3a,b are placed in the cranial vertebrae 10 such that the opening of the hook opens away from the caudal vertebra 12. Cam anchor 5a pre-threaded with longitudinal fixation elements 14b, is inserted into the caudal vertebrae 12. The covers over the cam-operated anchors 5a,b have been removed in FIG. 1C to expose the flexible longitudinal fixation elements 14a, b within the cams. Flexible elongate element 14b) is looped over the hook anchors 3a,b such that it is captured by the hooks 4a,b in anchors 3a,b. Once the flexible elongate element 14b is captured in hook 4a,b, tension is applied to the ends of flexible elongate element 14b that extend from cam anchor 5a to tighten it around hook anchors 3a,b and apply tension across the disc space between the cranial and caudal vertebrae 10, 12. Once sufficient tension has been applied to the flexible elongate element 14b, cam 6a is rotated into the locked position, as shown, to maintain tension on the flexible elongate element.

Cam anchors 5b, pre-threaded with longitudinal fixation elements 14a, is then inserted into the caudal vertebrae 12. The flexible elongate element 14a is looped over the hook 4a,b such that it is captured by the openings in anchors 3a,b. As shown in FIG. 1C, Cam 6b in cam-operated anchor 5b remains in the unlocked position such that the flexible elongate element 14a can slide freely through the anchor 5b. Once the flexible elongate element 14a is captured in hook anchors 3a,b, tension is applied to the ends of the flexible elongate element that extend from can anchor 5b to tighten it around hook anchors 3a,b and apply additional tension across the disc space between the cranial and caudal vertebrae 10, 12.

Tension can be applied to the ends of the flexible longitudinal fixation elements 14a,b before and while the cam 6a,b is rotated into the locked position. In some embodiments, the cam-operated anchors 5a,b may have anti-rotation features that prevent rotation of the cam into a position that loosens the hold on the ends of the flexible longitudinal fixation elements 14a,b. For example, an elastic or shape memory component could deploy against the side of the cam when it is rotated into the locked position, i.e., perpendicular to a longitudinal axis of the spine. In some embodiments, enlargements on the ends of the flexible longitudinal fixation elements 14a,b may cooperate with a tool that applies tension on the ends of the flexible longitudinal fixation element. The ends of the flexible longitudinal fixation elements 14a,b may be cut and removed after cams 6a,b are locked. The cam fastening mechanism preferably enables about 8 to about 40 pounds of tension to be applied to the flexible longitudinal fixation elements 14a,b. Alternatively, the cam mechanism enables about 7, about 6, or about 5 or less pounds of tension to be applied to the ends of flexible longitudinal fixation elements 14a,b. Alternatively, the cam mechanism enables about 41, about 42, about 43, about 44 or more pounds of tension to be applied to the ends of the flexible longitudinal fixation elements 14a,b.

As shown in FIG. 1B, the tension from flexible elongate elements 14a,b on the hooks 4a,b keeps the hook-like washer 7 from rotating about the head of the anchor and releasing the flexible elongate elements 14a,b. Alternatively, in some embodiments, the hooks 4a,b can be crimped after the flexible elongate elements 14a,b have been looped around them to further prevent the hooks 4a,b from releasing the flexible elongate elements. In some embodiments, as a cage or other intradiscal device 20 can be placed in between the cranial 10 and caudal 12 vertebrae after all or a portion of the disc has been removed. In addition, an in-growth component 16, such as a mesh patch made of polyester, polypropylene, allograft, autograft, xenograft, or other porous material as discussed further in co-pending patent application Ser. No. 11/945,994, entitled "Methods of Anterior Fixation and Stabilization of a Spinal Segment," filed on Nov. 27, 2007 hereby incorporated by reference in its entirety, can be placed between the flexible elongate elements 14a,b and the vertebrae 10,12 to act as scaffolding for connective tissue in-growth In one embodiment, the in-growth mesh patch 16 is attached to the anterior surface of cage 20. In-growth mesh 16 may also have extensions that may extend to cover the area between hook-like anchors 3a,b and cam-operated anchors 5a,b, as seen in FIG. 1C.

In some embodiments, a flexible spinal stabilization device can be used to stabilize multiple levels. As shown in FIGS. 2A-B, an alternative embodiment of the flexible stabilization system uses four cam-operated anchors 25a,b,c,ca,b and two hook anchors to join three adjacent vertebrae 10, 11 and 12, As shown in FIG. 2A, cam-operated anchors 25a-d were placed into the cranial 10 and caudal 12 vertebrae. Hook anchors 23a,b, each having at least two hooks associated with the enlarged head of the anchor, were placed into the intermediate vertebra 11. Each of the cam-operated anchors 25a-d was threaded with a flexible longitudinal fixation element 14a-d. In use, flexible longitudinal fixation elements 14a,b from cam-operated anchors 25a,b were looped around hooks 24a,c on hook-anchors 23a,b, tension was applied to the flexible longitudinal fixation elements 14a,b and the cams in anchors 25a,b were rotated into the locked position to form a cross-braced arrangement joining vertebrae 10,11. Flexible longitudinal fixation elements 14c,d from cam-operated anchors 25c,d were looped around hooks 24b,d on hook-anchors 23a,b, tension was applied to the flexible longitudinal fixation elements 14c,d and the cams in anchors 25c,d were rotated into the locked position to form a cross-braced arrangement joining vertebrae 11,12. As discussed above, in the cam anchors 25a-d can be pre-threaded with flexible longitudinal fixation elements 14a-d in a loose, looped configuration so that it is not necessary to thread the fixation elements through the cam anchor after they have been placed in the vertebrae.

As shown in FIG. 2C, the anchors 23a,b used for a flexible stabilization system joining multiple levels of vertebrae have at least two hooks 24a,b adapted to capture and retain the loops of flexible elongate elements extending from locking anchors, such as a cam-operated anchors 25a-d, in adjacent vertebrae both above and below. The hooks 24a,b extend from the anchor 23 at an angle with their openings facing inward such that the loops be captured and retained in the hooks 24a,b. As shown in FIG. 2B, opposing forces on hooks 24c,d from the tension on the fixation elements 14b,d keeps the anchor 23b from rotating which prevents the loops of the fixation elements from slipping out of the hooks 24c,d. In some embodiments, the hooks 24c,d can be crimped after the loops of the fixation elements have been captured to further prevent the loops from slipping out. In some embodiments, as shown in FIG. 2D, two or more hooks 24a,b can be joined together on a single washer 27 such that the hooks are fixed at a specific angle relative to one another. For example, washer 27 has two hooks 24a,b located on opposite ends of the washer with openings facing the center of the washer for receiving loops of the longitudinal fixation elements. The washer is preferably about 4 to 8 mm long, about 3 to 6 mm wide and similar in height to the washer described in FIG. 1D. Alternatively, the washer could be about 1, about 2, about 3, about 9, about 10, or about 11 mm long or longer, and about 1, about 2, about 7, about 8, about 9 mm wide or wider. In alternative embodiments, each hook 24a,b can be provided on a separate washer located below the head of the anchor and thus can rotate with respect to one another.

In some embodiments, locking anchors having an adjustable cable tie strap component pre-threaded with a fixed looped suture, or longitudinal fixation element, can be used in combination with the hook anchors to provide a flexible stabilization system for stabilizing two or more adjacent vertebrae. As shown in FIG. 3C, locking anchor 45 has a first portion, such as a screw, adapted to be inserted into a vertebra. The second portion, adapted to engage a longitudinal fixation element includes a cable tie-like strap 40 slidably inserted through a receptacle 46 on the head of the anchor 45. The cable tie-like strap has gear rack 41, such as plurality of horizontal ribs extending the length of the cable tie-like strap, which is configured to frictionally engage corresponding ribs or teeth of a ratchet mechanism in the receptacle 46 on the head of the anchor 45. The ratchet mechanism engages the rack 41 of the cable-tie strap as it is pulled through the receptacle 46 and prevents it from sliding backwards such that tension on the cable-tie strap 40 can be maintained. A flexible elongate element 14 is threaded through a hole on the end of the cable tie-like strap 40 and the ends of the flexible longitudinal fixation element 14 are fastened to each other to form a band or loop. The ends of the flexible longitudinal fixation elements are preferably fastened to each other during the manufacturing process, for example by welding or crimping. The locking anchors 45 are provided pre-threaded with suture loops, or bands, in a range of sizes to accommodate different regions of the spine, different size intadiscal devices and to provide options for the appropriate amount of tension across adjacent vertebrae in use. The suture loops are preferably 1 to 3 millimeters wide and 1 to 3 millimeters long. Alternatively, the suture loops could be less than 1, or 4, 5, or more millimeters wide or tall in alternative embodiments of the invention. The length of the cable tie strap 40 is also selected such that when it is fully extended from the receptacle 46 it the loop or band of the longitudinal fixation element will have sufficient slack to enable a surgeon to place the loop around hook anchors in an adjacent vertebrae. Once the loop has been placed around the hook anchors, the cable tie-like strap 40 can then be pulled through the ratchet mechanism to tighten the loop around the hook anchors and apply the needed tension across the anchors. The excess cable tie strap protruding from the opposite end of the receptacle can then be cut off and removed.

Figure 3A:
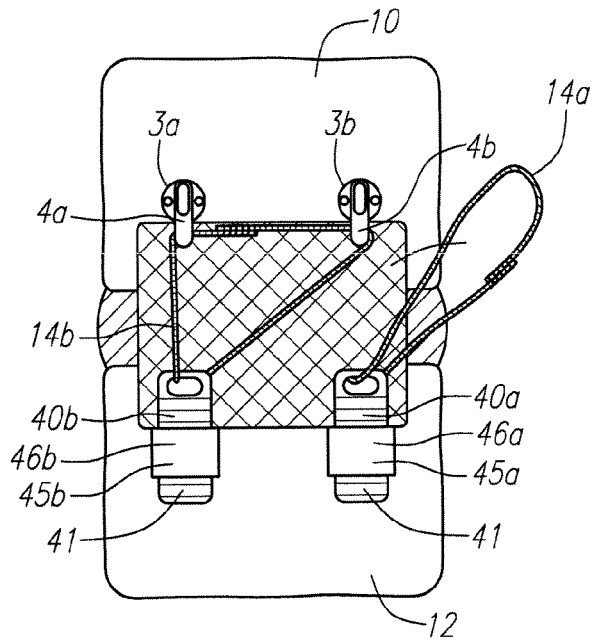
FIG. 3A is an anterior view of a portion of the spine and al alternative embodiment of the invention.
Figure 3B:
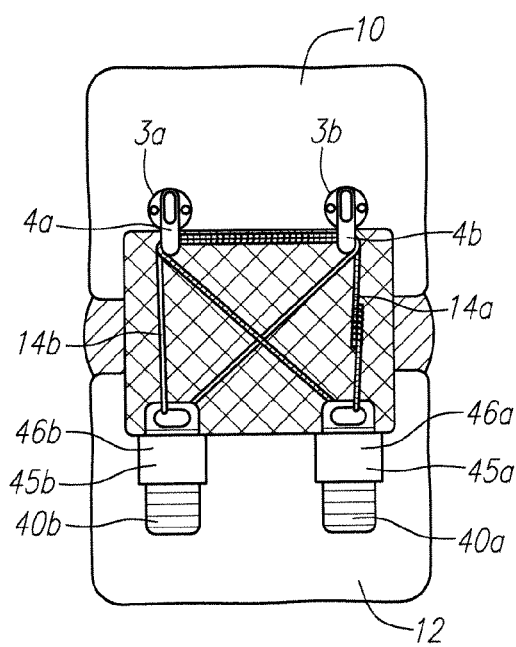
FIG. 3B is an anterior view of a portion of the spine and the embodiment drawn in FIG. 3A.
Figure 3C:
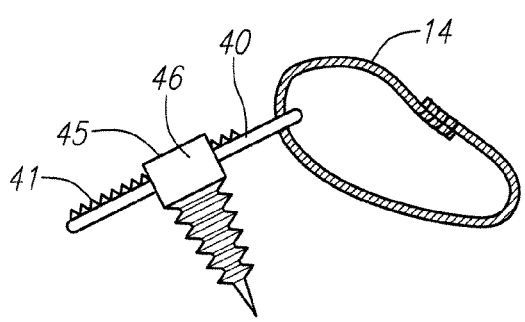
FIG. 3C is a lateral view of the anchor and longitudinal fixation element illustrated in FIGS. 3A-B.

In use, as shown in FIGS. 3A-B, locking anchor 45b is inserted into caudal vertebra 12 with flexible longitudinal fixation element 14b extending from cable tie-like strap 40b in a looped configuration. Flexible longitudinal fixation element 14b is inserted into the hook-like anchors 3a,b in the cranial vertebra 10. Once flexible longitudinal fixation element 14b is captured by hooks 4a,b, cable tie-like strap 40b is pulled through receptacle 46b to tighten flexible longitudinal fixation element 14b around hook anchors 3a,b and to apply tension across the anchors 3a,b and 45b. A cable tie tension tool may be used to advance the strap 40b through the receptacle 46b of the anchor 45b. Advancing the cable tie-like strap through the receptacle applies tension to the flexible longitudinal fixation element. The excess cable tie-like strap 40a is then cut off and removed after the strap is advanced through the receptacle. Next, locking anchor 45a is inserted into caudal vertebra 12 with flexible longitudinal fixation element 14a extending from cable tie-like strap 40a in a looped configuration. Flexible longitudinal fixation element 14a is inserted into the hook-like anchors 3a,b in the cranial vertebra 10. Once flexible longitudinal fixation element 14b is captured by hooks 4a,b, cable tie-like strap 40a is pulled through receptacle 46b to tighten flexible longitudinal fixation element 14b around hook anchors 3a,b and to apply tension across the anchors 3a,b and 45a, thus applying additional tension across the disc space between the cranial and caudal vertebrae 10, 12. In some embodiments, two or more loops of longitudinal fixation element can be provided with a single locking anchor such that an additional longitudinal fixation element can be placed around the hook anchors in an adjacent vertebrae to apply additional tension across the disc space. In addition, the longitudinal fixation element material can be selected to be more or less flexible to provide the needed tension across the anchors.

The cable tie-like fastening components preferably have a tensile strength of about 20 to 80 pounds. Alternatively, the cable tie-like fastening components may have a tensile strength of 19, 18, 17, 16 pounds or less. Alternatively, the cable tie-like fastening components may have a tensile strength of 81, 82, 83, 84, 85 pounds of more. The straps of the cable tie-like components are preferably made of nylon, polyethylene, polypropylene, or other biocompatible material. The straps are preferably 1 to 3 mms wide and 0.5 to 2 mms thick. Alternatively, the straps could be 0.9, 0.8, 0.7, 0.6 mm wide or less wide. Alternatively, the straps could be 3.1, 3.2, 3.3, or 3.4 mm wide or wider. Alternatively, the straps could be 0.4, 0.3, or 0.2 mm thick or thinner. Alternatively, the straps could be 2.1, 2.2, 2.3, or 2.4 mm thick or thicker. The straps are preferably about 6 to 10 mm long. Alternatively, the straps could be 5, 4, or 3 mm long or shorter. Alternatively, the straps could be about 11, 12, 13, or 14 mm long or longer.

Figure 4A:
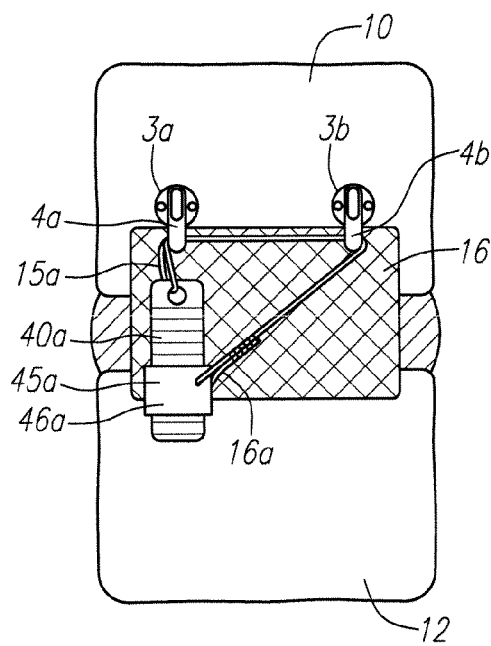
FIG. 4A is an anterior view of a portion of the spine and an alternative embodiment of the invention.
Figure 4B:
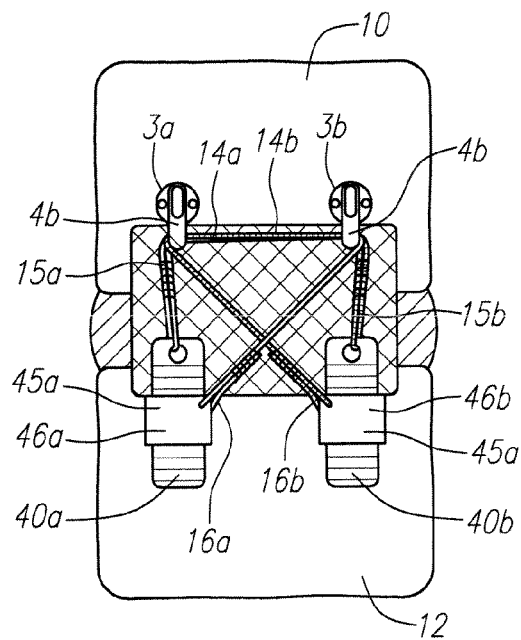
FIG. 4B is an anterior view of a portion of the spine and the embodiment illustrated in FIG. 4A.

In some embodiments, alternative methods may be used to fasten the flexible longitudinal component to the cable tie-like strap. For example, the components could be welded together. Alternatively, the strap component could have a first end that cooperates with the receptacle of the anchor and a second end with one or more strands that form the flexible longitudinal fixation element. As shown in FIG. 4A, in one embodiment, the first end of the flexible longitudinal fixation element 15a is attached to the cable tie-like strap 40a. The second end of the flexible longitudinal fixation element 16a is attached to the receptacle 46a of the cable tie-like anchor 45a. The device is preferably manufactured as described in FIG. 3A.

As described with reference to FIGS. 3A-B, the cable tie-like anchors 45 are selected with a pre-sized lengths of longitudinal fixation element 14a,b attached to the anchors 45a,b based on the location of the vertebrae to be joined. The cable tie-like straps 40a,b fully extend from the receptacles 46a,b to provide a maximum diameter loop of longitudinal fixation element 14a,b for extending around hook anchors 3a,b. Once the longitudinal fixation elements 14a,b have been placed around hooks 4a,b, tension can be applied to the flexible longitudinal fixation elements 14a,b by advancing the straps 40a,b through the receptacles 46a,b.

Figure 5A:
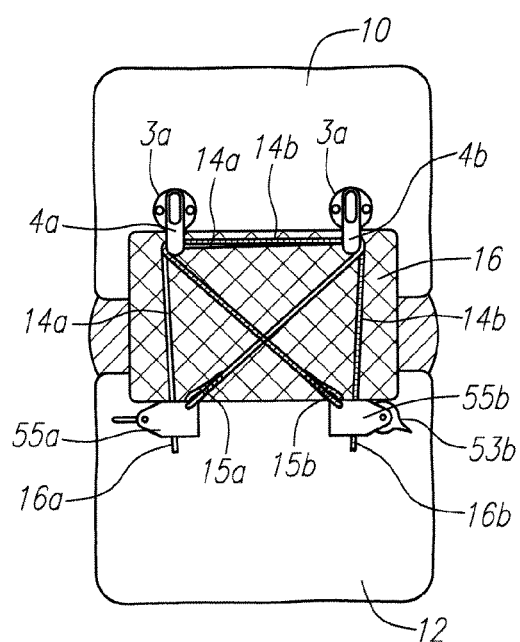
FIG. 5A is an anterior view of a portion of the spine and an alternative embodiment of the invention.
Figure 5B:
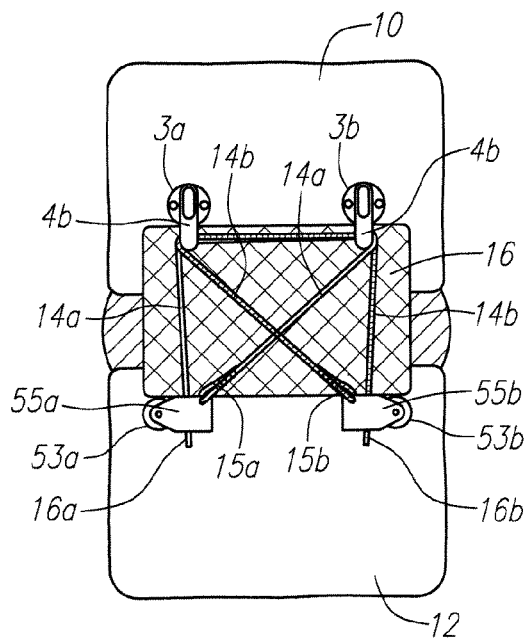
FIG. 5B is an anterior view of a portion of the spine and the embodiment illustrated in FIG. 5A.

An alternative embodiment of a locking or tensioning anchor for use in combination with one or more hook anchors to provide a flexible stabilization system for stabilizing two or more adjacent vertebrae is shown in FIGS. 5A-B. Here, the first end 15a,b of a flexible longitudinal fixation element 14a,b was fastened to an anchor 55a,b during the manufacturing process. The second end 16a,b of the flexible longitudinal fixation element 14a,b was passed through an opening or passage in the anchor 55a,b. A cam lock component 53a,b is configured to engage the portion of the longitudinal fixation element 14a,b in the passage in order to fasten the second end 16a,b of the longitudinal fixation element 14a,b to the anchor 55a,b. Cam lock anchors can advantageously provide an infinite range for tightening longitudinal fixation elements around hooks anchors enabling finer variations on the tension applied across the vertebrae compared with alternative embodiments which provide a fixed number of incremental steps for adjusting the longitudinal fixation elements. In use, anchors 55a,b are placed in the caudal vertebra 12 with the longitudinal fixation elements 14a.b in a loose loop configuration having enough slack for the surgeon to place the loops around hook anchors 3a,b. Cam components 53a,b are rotated into an open position to allow the second ends 16a,b of the longitudinal fixation elements 14a,b to slide freely through the passages in anchors 55a,b. Once the loops have been captured by hooks 4a,b, the second ends 16a,b of the longitudinal fixation elements 14a,b are pulled through the passages in the anchors to apply tension across the vertebrae 10, 12. Cam components 53a,b are then rotated into the locked position, as shown in FIG. 5B to engage the second ends of the longitudinal fixation elements 14a,b and maintain tension across the vertebrae 10,12.

Figure 6A:
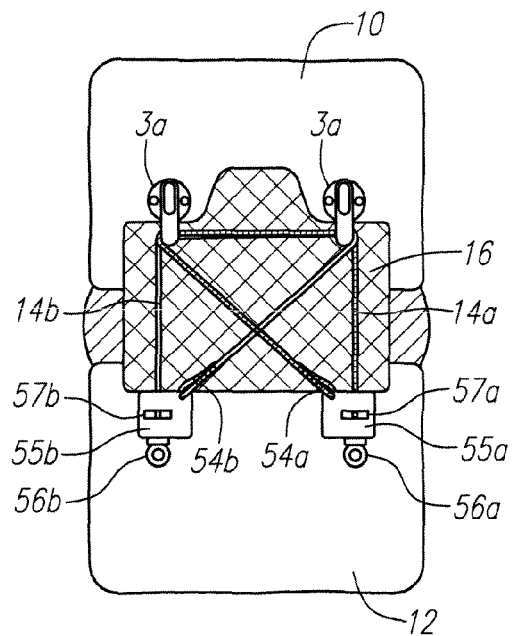
FIG. 6A is an anterior view of a portion of the spine and an alternative embodiment of the invention.
Figure 6B:
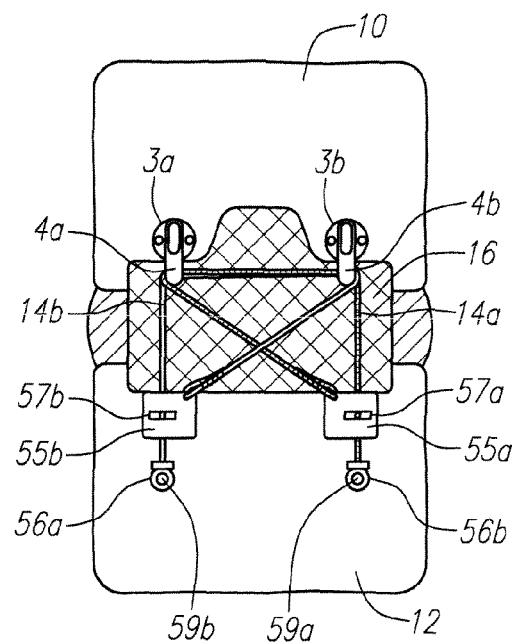
FIG. 6B is an anterior view of a portion of the spine and the embodiment illustrated in FIG. 6A.
Figure 6C:
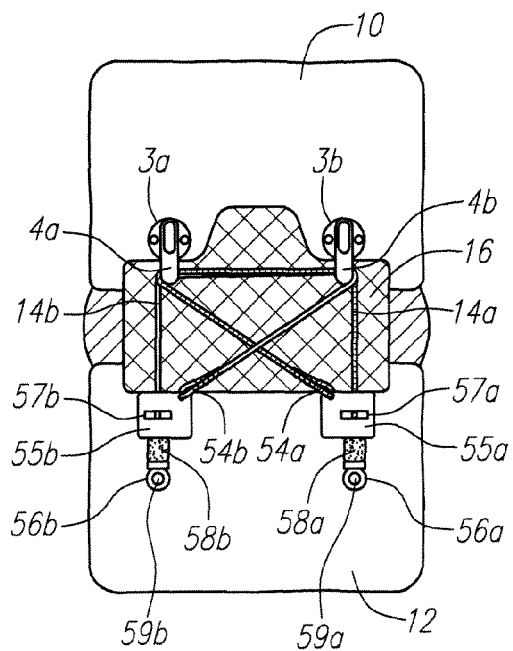
FIG. 6C is an anterior view of a portion of the spine and the embodiment illustrated in FIG. 6B.
Figure 6D:
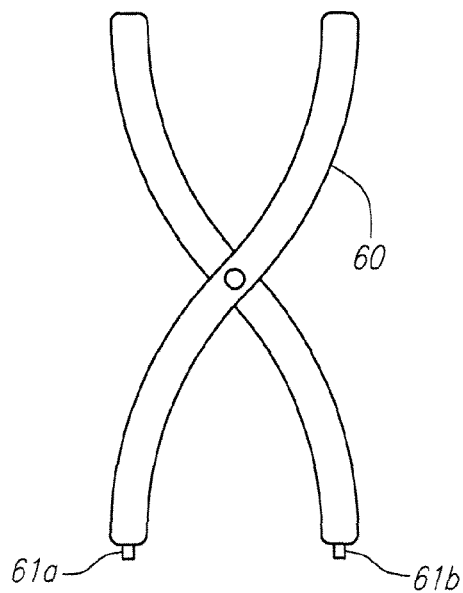
FIG. 6D is an embodiment of a tensioning tool for use with the anchors illustrated in FIGS. 6A-C.

In an alternative embodiment, as shown in FIGS. 6A-C, locking anchors 55a,b may utilize one or more spacers 58a,b to maintain tension across the spinal stabilization device. Here, as described above, the first ends 54a,b of flexible longitudinal fixation elements 14a,h are fastened to anchors 55a,b during the manufacturing process. The second ends 56a,b of the flexible longitudinal fixation elements 14a,b are passed through an opening or passage in the anchors 55a,b. The second ends 56a,b can be enlarged and optionally have openings or holes 59a,b for engaging a tensioning tool such as the tool 60 shown in FIG. 6D. In some embodiments, anchors 55a,b can also have openings 57a,b for engaging tensioning tool 60.

In use, anchors 55a,b are placed in the caudal vertebra 12 with the longitudinal fixation elements 14a.b pre-threaded through anchors 55a,b in a loose loop configuration having enough slack for the surgeon to place the loops around hook anchors 3a,b as shown in FIG. 6A. Once the loops have been captured by hooks 4a,b, the second ends 56a,b of the longitudinal fixation elements 14a,b are pulled through the passages in the anchors 55a,b to apply tension to the longitudinal fixation elements 14a,b, as shown in FIG. 6B. In some embodiments, tips 61a,b of tool 60 can be inserted into opening 57a,b on top of the anchors 55a,b and opening 59a,b on longitudinal fixation element 14a,b to advance the fixation elements through anchors 55a,b and apply tension across the anchors. Handles of tool 60 extend outside of the body such when the handles are brought together, tips 61a,b will diverge, pulling the enlarged ends 59a,b of the longitudinal fixation elements 14a,b through anchors 55a,b.

As shown in FIG. 6C, once adequate tension has been applied to second ends 54a,b of the longitudinal fixation elements 14a,b, spacer components 58a,b are placed over the excess flexible longitudinal fixation elements between the anchors 55a,b and the enlarged ends 59a,b of the longitudinal fixation elements 14a,b to prevent the longitudinal fixation elements from slipping back through the anchors 55a,b in order to maintain the tension on the longitudinal fixation elements 56a,b. In some embodiments, deformable spacer components may be crimped over the flexible longitudinal fixation elements. In other embodiments, alternative mechanisms may be used to fasten the spacers 59a,b to the flexible longitudinal fixation elements 14a,b. The spacer components may be made of elastic, super elastic, or shape memory materials. For example, Nitinol spacer components could be fastened to the flexible longitudinal fixation components. The elasticity of the spacer and the shape memory property of the spacer could cause the spacer to grasp the flexible longitudinal fixation element. The spacer components 58a,b are preferably supplied in various sizes to fit the space between the anchor 55a,b and the enlarged ends of the flexible longitudinal fixation. For example, the spacers could be supplied in 2 to 10 mm lengths. Alternatively, the spacers could be about 1, about 11, about 12, about 13, or about 14 mm long or longer. In some embodiments, one spacer may be used between each of the anchors 55a,b and enlarged ends 59a,b of the longitudinal fixation elements 14a,b. Alternatively two or more spacers could be used between the anchors and enlarged ends of the longitudinal fixation elements to provide more flexibility in the amount of tension applied to the longitudinal fixation elements. The spacers are preferably about 2 to about 4 mm wide. Alternatively, the spacers could be about 1, about 5, about 6, about 7 mm wide or wider. The height of the intradiscal device or the intervertebral disc is used to select the anchor with optimal length of flexible longitudinal fixation element. For example, a device with a 50 mm flexible longitudinal fixation element may be preferred for use with 10 mm tall intradiscal cages. Alternatively, a device with about 49, about 48, about 47, about 46 mm or less long flexible longitudinal fixation elements may be preferably used with cages 10 mm tall. Alternatively, a device with about 51, about 52, about 53, about 54, about 55, about 56, about 57, about 58 mm or longer flexible longitudinal fixation elements may preferably used with cages about 10 mm tall. Devices with longer flexible longitudinal fixation elements are preferably used with cages taller than 10 mm. For example, a device with a 54 mm may be optimal for use with cages about 12 mm tall. Devices with shorter longitudinal fixation elements are preferably used with cages smaller than about 10 mm. For example, a device with a 41 mm may be optimal for use with cages about 6 mm tall.

In an alternative embodiment of a flexible stabilization system, the locking anchor 35a,b can be preassembled with a longitudinal fixation element having a slotted component attaching the fixation element to the anchor. As shown in FIGS. 7A and 7C the first ends 15a,b of the flexible longitudinal fixation elements 14a,b are fastened to anchors 35a,b as described above. The second ends 16a,b of the flexible longitudinal fixation elements 14a,b are fastened to slotted components 30a,b. The underside of the slotted components 30a,b have teeth 17 configured to engage corresponding teeth 37 on the heads of anchors 35a,b. Slotted components 30a,b are then placed over a threaded post protruding from the heads of anchors 35a,b, as shown in FIG. 7C. Nuts 36a,b are placed on the threaded post of the anchors 35a,b to attach the slotted components 30a,b to the anchors 35a,b while still leaving adequate space between the teeth of the anchor 37 and the teeth 17 on the slotted components 30a,b to enable the slotted components 30a,b to be advanced over the anchors 35a,b. In some embodiments, the anchors are push in anchors. In alternative embodiments, the slotted portion can be configured to rotate around the threaded post on the heads of the anchor and therefore the anchor can be a screw anchor In use, as shown in FIGS. 7A-B, anchors 35a,b are placed in the caudal vertebra 12 with slotted ends 30a,b of fixation elements 14a.b attached to anchors 35a,b in a loose loop configuration having enough slack for the surgeon to place the fixation elements 14a,b around hook anchors 3a,b as shown in FIG. 7A. The fixation elements 14a,b are placed in hooks 4a,b and then the slotted ends 30a,b are advanced over anchors 35a,b to apply tension to the longitudinal fixation elements 14a,b, as shown in FIG. 7B. Once the desired amount of tension has been placed on the longitudinal fixation elements 14a,b, nuts 36a,b are tightened to lock the teeth 17 on the slotted components 30a,b between the teeth 37 on anchors 35a,b, as shown in FIG. 7D, in order to maintain the tension on the fixation elements 14a,b.

FIGS. 8A-D illustrate an alternative embodiment of a locking anchor 65a,b preassembled with a longitudinal fixation element 14a,b. Here, as shown in FIG. 8A, the ends of a flexible longitudinal fixation elements 14 extend through one or more passages in the anchor 65a,b. Screw 62a-d course through a threaded bore in the anchors 65a,b perpendicular to the flexible longitudinal fixation element 14a,b. The passages 64 extend along an axis perpendicular to portions of the anchors that are inserted into the bone, i.e., the screw portion 66. Each anchor 65a,b may have one, two, three, or more passages 64. In use, once the longitudinal fixation element 14 has been advanced through the passage 64, screw 62 will be tightened to hold the longitudinal fixation element 14 in place against the wall of the passage and thereby maintain the tension on the longitudinal fixation element 14 as shown in FIG. 8D. In some embodiments, the ends of the flexible longitudinal fixation element 14 may be enlarged and may contain openings configured to cooperate with a tensioning tool, such as the tensioning tool 170 shown in FIG. 12, to apply tension on the flexible longitudinal fixation elements. In some embodiments, both ends of the longitudinal fixation element may have enlarged ends for cooperating with a tensioning tool, such that tension can be applied to either end of the longitudinal fixation element as friction over the hook anchors is encountered.

The enlarged portion 18a,b of the flexible longitudinal fixation element 14 are preferably fastened to the flexible longitudinal fixation elements 14a,b after the ends of the flexible longitudinal fixation elements 14a,b are advanced through holes in the anchors 65a,b. For example, enlarged components 18a,b could be welded to the ends of the flexible longitudinal fixation elements. The enlarged components 18a,b are preferably applied to the ends of the flexible longitudinal fixation elements 14 during the manufacturing process. Alternative mechanisms may be used to enlarge the end of the flexible longitudinal fixation elements. For example, the ends of the flexible longitudinal fixation elements could be knotted. Alternatively, as described with respect to FIGS. 6A-D, deformable components could be crimped to the ends of the flexible longitudinal fixation elements. In some embodiments, the ends of the flexible longitudinal fixation elements could be treated to resist wear by the screws. For example, polyethylene, polypropylene, nylon or other material could be molded over the ends of the flexible longitudinal fixation elements. The distal 5 to 15 mm of the ends of the flexible longitudinal fixation elements preferably receive such treatment. Alternatively, the distal 4, 3, 2, or 1 mm of the flexible longitudinal fixation elements could receive such treatment. Alternatively, the distal 16, 17, 18, 19 mm or more of the flexible longitudinal fixation elements could receive such treatment. Alternatively, the entire flexible longitudinal fixation elements could receive such treatment.

In use, anchors 65a,b are placed in the caudal vertebra 12 with fixation elements 14a.b threaded through passages in anchors 35a,b in a loose loop configuration having enough slack for the surgeon to place the fixation elements 14a,b around hook anchors 3a,b as shown in FIG. 8A. The fixation elements 14a,b are placed in hooks 4a,b the ends 18a-d of the flexible longitudinal fixation elements 14a,b were advanced through the passages in the anchors 65a,b to apply tension to the longitudinal fixation elements 14a,b, as shown in FIG. 7B. Once the desired amount of tension was placed on the longitudinal fixation elements 14a,b, screws 62a-d on the top of the anchors 65a,b were advanced into the anchors 65a,b through the threaded bores to hold and maintain tension on fixation elements. As seen in FIG. 8C, a sagittal cross section of the anchor, the threaded bore adapted to engage the screw 62 communicates with passage 64 housing the elongate element 14. The tips of the screws 62a-d were advanced through passage 64 and into the flexible longitudinal fixation elements 14a,b to fasten the flexible longitudinal fixation elements 14a,b to the anchors 65a,h. The ends of the flexible elongate elements 18a-d were cut and removed after fastening the flexible elongate elements 14a,b to the anchors 65a,b through the screws 62a-d.

In some embodiments, as shown in FIGS. 8B and 8D, the screws 62a-d were advanced until the shaft of the screws broke and then the heads of the screws were removed. This configuration assures sufficient torque was applied to the screw to fasten the flexible longitudinal fixation element 14 to the anchor 65. The configuration also results in a very low profile device. The head of the screw 62 is removed at the completion of the procedure. Headless set-screws could be used in other embodiments of the invention. Alternative mechanisms may be used to fasten the ends of the flexible longitudinal fixation elements to the anchors. For example, the anchors could be crimped over the ends of the flexible longitudinal fixation elements.

Figure 9:
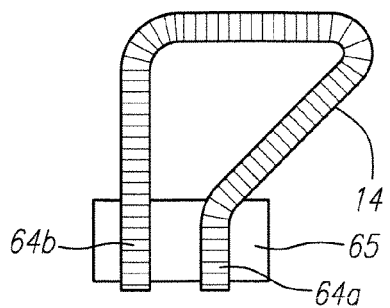
FIG. 9 is an axial cross-section of the anchor and longitudinal fixation element illustrated in FIG. 8A.
Figure 10A:
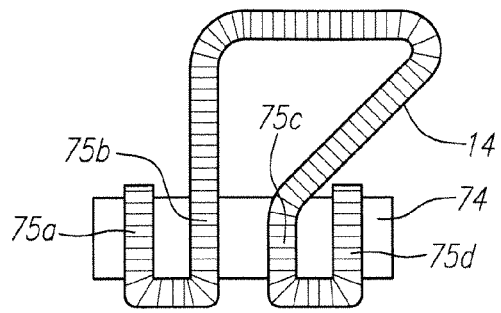
FIG. 10A is an axial cross-section of an alternative embodiment of an anchor and longitudinal fixation element.
Figure 10B:
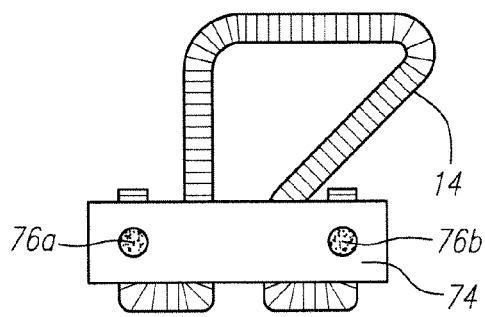
FIG. 10B is a top view of the anchor and longitudinal fixation element illustrated in FIG. 10A.

As discussed above the ends of the longitudinal fixation elements can be threaded through one or more passages in the locking anchors 65. For example, as shown in FIG. 9, anchor 65 has two passages 64a,b extending along an axis generally perpendicular to the screw portion of the anchor 65 that are adapted to receive the ends or end regions of the elongate element 14 there through. Here, each end of the longitudinal fixation element is threaded through one passage in the anchor. In an alternative embodiment, as shown in FIG. 10A-B, anchor 74 has four passages 75a-d, each extending along an axis generally perpendicular to the screw portion of the anchor that are adapted to receive the ends or end regions of the elongate elements there through. The anchor 74 can be pre-threaded with each end of the flexible longitudinal fixation element 14 passed through two passages 75a,b and 75c,d. In use, as described above with respect to FIGS. 8A-D, once tension has been applied to the ends of the longitudinal fixation elements, screws 76a,b will be advanced into threaded bores in anchor 74, through passage 75a,d and into the ends of the longitudinal fixation element 14 to hold the fixation element in place against the walls of passages 75a,d. The configuration of the flexible longitudinal fixation element though passages 75a-d in anchor 74 increases the force required to apply tension to the flexible longitudinal fixation element but reduces the force required by the screws 76*a,b* to maintain tension on the flexible longitudinal fixation element when compared to the configuration drawn in FIG. 9.

Figure 18A:
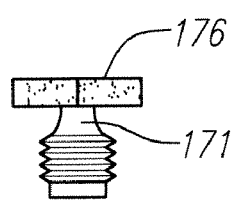
FIG. 18A is a lateral view of an embodiment of a screw for use with the anchor illustrated in FIG. 15A.
Figure 18B:
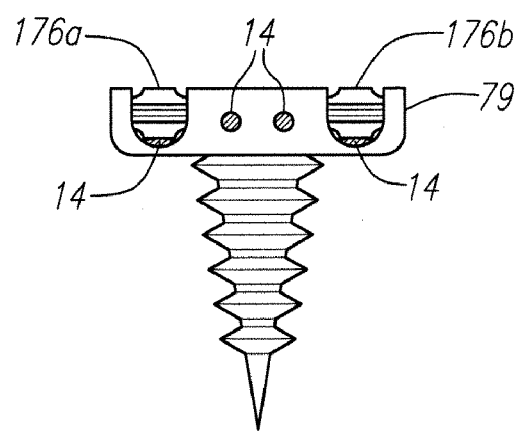
FIG. 18B is a coronal cross-section illustrating the anchor in FIG. 15A with the screw illustrated in FIG. 18B.

FIG. 18A is a lateral view of an alternative embodiment of a screw for use with anchors described herein. The screw 176 has a stress riser 171 which facilitates shearing of the screw head. As shown in FIG. 18B, screws 176*a,b* were advanced into the anchor 79 and sheared. The screws 176*a,b* force the flexible longitudinal fixation element 14 against the bottom of the passages in the anchor, holding the flexible fixation element in place and thereby maintaining tension on the flexible fixation element. The threads of the screw 176 and the stress riser 171 are preferably recessed within the bore in the anchor 79.

Figure 11A:
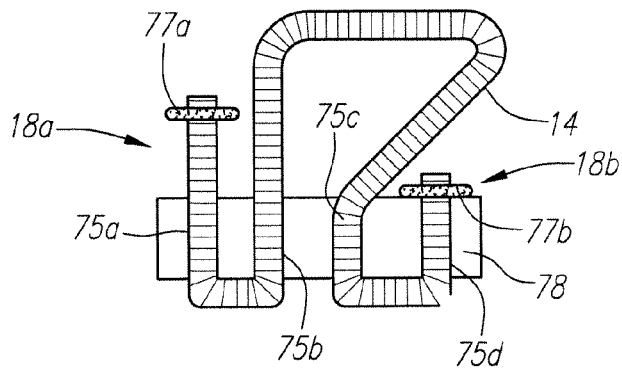
FIG. 11A is an axial cross-section of an alternative embodiment of the anchor and longitudinal fixation element illustrated in FIG. 10A.
Figure 11B:
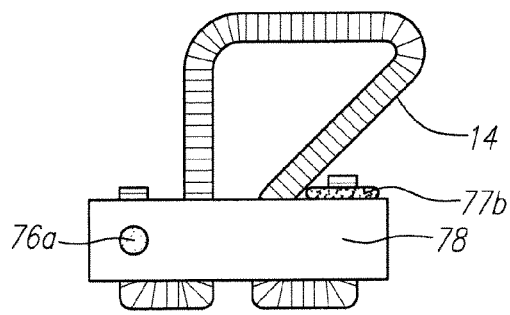
FIG. 11B is a top view of the anchor and longitudinal fixation element illustrated in FIG. 11A.

FIG. 11A is an axial cross section of an alternative embodiment of the anchor 78 and flexible longitudinal fixation element 14 drawn in FIG. 10A. The ends 77*a,b* of the flexible longitudinal fixation element 14 are enlarged. The enlarged components 77*a,b* are preferably fastened to the ends of the flexible longitudinal fixation elements 14 after the flexible fixation element 14 is passed through the holes in the anchors 74 as described with respect to FIG. 8A. In use, as shown in FIG. 11B, fixation element 14 is advanced though the passages in anchor 78 such that enlarged end 77*a* of the fixation element engages the side wall of the anchor 78 eliminating the need for using a screw to fix one end of the fixation element. Further tension is then applied to the end of flexible longitudinal fixation element drawn on the left side of the drawing to engage hook anchors in an adjacent vertebrae and tighten the loop of the fixation element around the hook anchors, as described in reference to FIGS. 8A-B. Once the desired tension has been applied to the fixation element, screw 76*a* is advanced into threaded bore in anchor 78, through passage 75*a* and into the end of the longitudinal fixation element 14 to hold the fixation element in place against the walls of passages 75*d*. The end of the flexible longitudinal fixation element 14 distal to the screw was cut and removed. Unlike the embodiment drawn in FIG. 10B, a single screw 76*a* holds the flexible longitudinal fixation element in the anchor 78.

Figure 25:
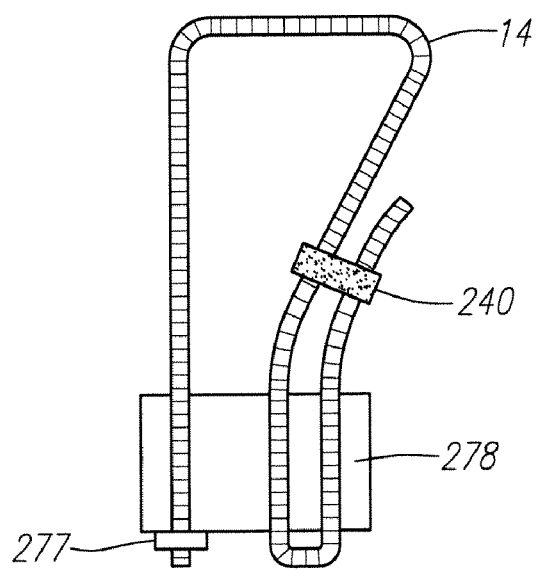
FIG. 25 is an axial cross-section of an alternative embodiment of an anchor and attached longitudinal fixation element

FIG. 25 illustrates an alternative embodiment of a locking anchor 278 and longitudinal fixation element 14 for use in the flexible stabilization systems described herein. The proximal end of the flexible longitudinal fixation element 14 is passed through two passages in the anchor and a fastening component 240. The distal end of the flexible longitudinal fixation element is enlarged 277. In use, as described above with respect to FIGS. 11A-B, fixation element 14 is advanced though the passages in anchor 278 such that enlarged end 277 of the fixation element engages the side wall of the anchor 278 eliminating the need for using a screw to fix one end of the fixation element. Tension is then applied to the proximal end of the flexible longitudinal fixation element 14 and the fastening component 240 is crimped, welded, or otherwise fastened to the flexible longitudinal fixation element 14 to maintain tension on the fixation element 14.

Figure 12:
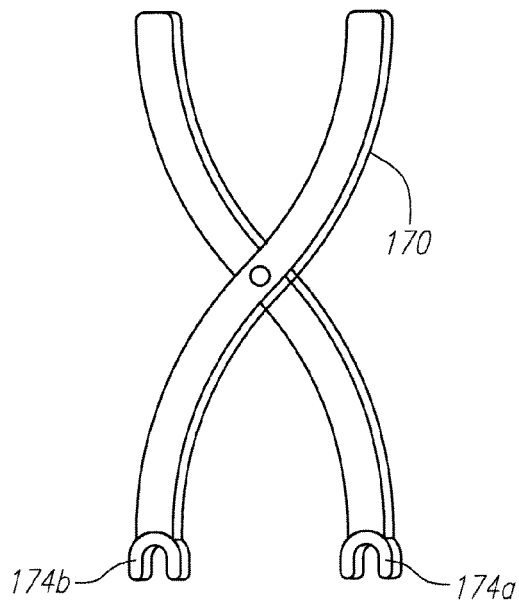
FIG. 12 is an oblique view of is an embodiment of a tensioning tool for use with the anchors illustrated in FIGS. 11A-B.

FIG. 12 is an oblique view of a tool 170 that may be used to apply tension to the flexible longitudinal fixation element 14 drawn in FIG. 11A. The tips 174*a,b* of the distracting tool are placed between the anchor 78 and the enlarged component 77*a* on the distal end of the flexible longitudinal fixation element 14. In use the tips of the distracting tool are placed around the longitudinal fixation element such that one tip 174*a* is pressed against the sidewall of the anchor 78 and the other tip 174*b* is pressed against the enlarged component 77*a* of the fixation element 14. When the handles are pulled together, the tip 174*b* engaging the enlarged component 77*a* will pull the fixation element 14 with it as it is expanded away from the anchor 78.

Figure 13A:
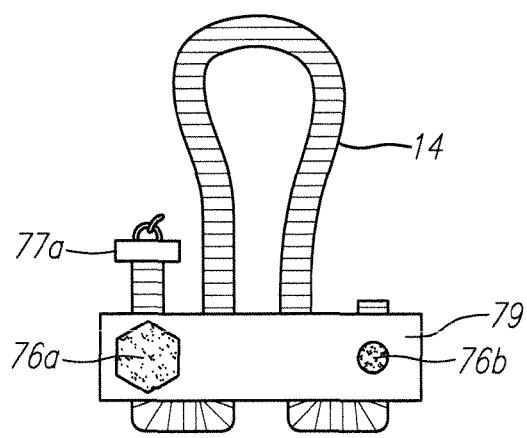
FIG. 13A is a top view of an alternative embodiment of an anchor and longitudinal fixation element.
Figure 13B:
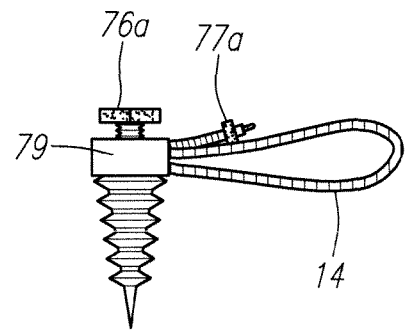
FIG. 13B is a lateral view of the anchor and longitudinal fixation element illustrated in FIG. 13A.
Figure 14A:
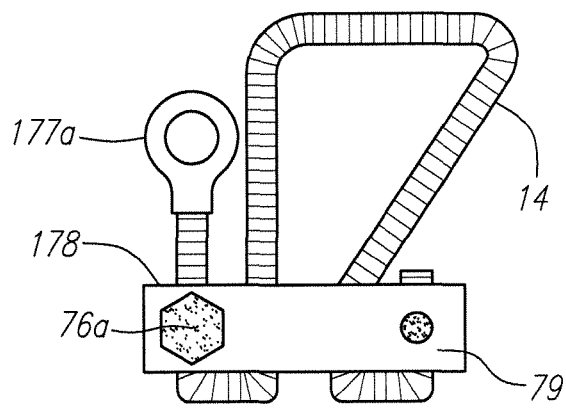
FIG. 14A is a top view of an alternative embodiment of an anchor and longitudinal fixation element.
Figure 14B:
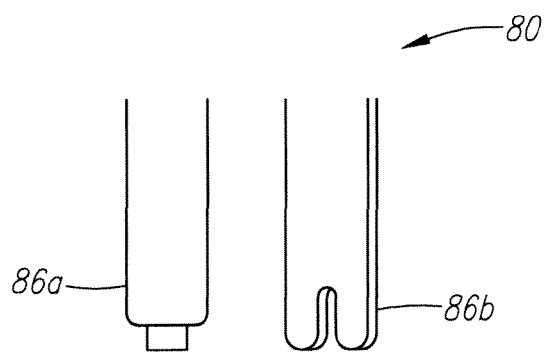
FIG. 14B is an oblique view of the tips of a distracting tool for use with the anchor illustrated in FIG. 14A.

FIGS. 13A-B illustrate an alternative embodiment of the anchor and flexible longitudinal fixation element drawn in FIG. 10B. The screw 76*b* in the left side of the anchor 79 was advanced into the anchor and sheared prior to insertion in the spine. The device is preferably supplied to surgeons with the screw 76*b* sheared. Like the embodiment of the invention drawn in FIG. 11A, the configuration permits surgeons to fasten the flexible longitudinal fixation element 14 to the anchor 79 by tightening a single screw 76*a*. In some embodiments, as shown in FIG. 14A, the enlarged end of the flexible longitudinal fixation element 14 has an opening 177*a* configured to receive one of the tips 86*a* of the distracting tool drawn in FIG. 14B. In use, the projection 86*a* from the first end of the tool fits into the opening 177*a* in the end of the flexible longitudinal fixation element 14. The second end 86*b* of the tool fits against the side 178 of the anchor 79 and straddles the portion of the flexible longitudinal fixation element 14 that lies between the distal end of the flexible element and the anchor. s described above, with respect to FIG. 12, when the handles are pulled together, the tip 86*a* engaging the enlarged component 177*a* will pull the fixation element 14 with it and through the passage in tip 86*b* as it is expanded away from the anchor 79, thereby applying tension to the longitudinal fixation element 14.

Figure 15A:
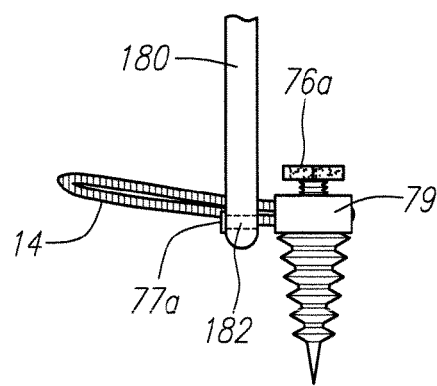
FIG. 15A is a lateral view illustrating a tensioning tool used to apply tension to a longitudinal fixation element and anchor.
Figure 15B:
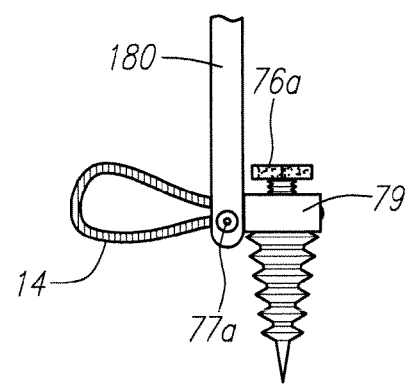
FIG. 15B is a lateral view of the anchor, longitudinal fixation element and tensioning tool in FIG. 15A illustrating the tensioning tool rotated to apply tension to the longitudinal fixation element.
Figure 15C:
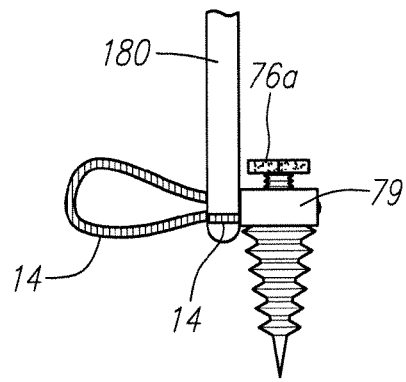
FIG. 15C is a lateral view of the anchor, longitudinal fixation element and tensioning tool in FIG. 15B illustrating the tensioning tool further rotated to apply tension to the longitudinal fixation element.
Figure 15D:
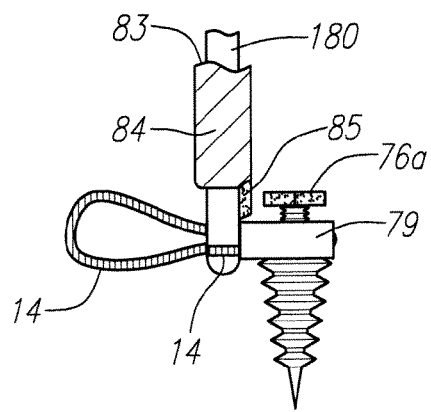
FIG. 15D is a lateral view of the anchor, longitudinal fixation element and tensioning tool in FIG. 15C and a cutting tool fit over the tensioning tool to sever the longitudinal fixation element.

FIG. 15A is a lateral view of the anchor 79 and flexible longitudinal fixation element 14 drawn in FIG. 13A and a lateral view of an alternative tensioning tool 180. The distal end of the flexible longitudinal fixation element 14 was passed through a hole or passage 182 in the tip of the tensioning tool 180. An enlarged component 77*a* was fastened to the distal end of the flexible longitudinal fixation element 14 after the end was passed through the passage 182 in the tensioning tool 180. As shown in FIG. 15B, the tensioning tool 180 was rotated relative to the anchor 79. Rotation of the tensioning tool pulls the flexible longitudinal fixation element 14 through the passage in the anchor 79. As shown in FIG. 15C, the tensioning tool 80 was rotated further than the tool drawn in FIG. 15B, such that elongate element 14 is beginning to wrap around an outer surface of the tensioning tool 80. Once the desired amount of tension has been applied, by rotating the tensioning tool, a cutting tool 84 is advanced over the tensioning tool 180, as shown in FIG. 15D. The cutting tool 84, an elongate tubular member having a lumen 83 there through, fits over the shaft of the tensioning tool 180 and has at least one sharp edge 85 located at the distal end of the cutting tool 84 that is adapted to sever the elongate element 14. The cutting tool 84 is advanced over the shaft of the tensioning tool 80 to cut the flexible longitudinal fixation element 14 after the screw 76*a* on the top of the anchor 78 is tightened.

In some embodiments, as shown in FIG. 16A, the cutting tool 184 can have notch 188 on the distal end for severing the fixation element 14. The flexible longitudinal fixation 14 element passes from the tensioning tool 180 and through a notch 188 in the cutting tool 184. At least one side of the notch 188 in the cutting tool 184 is sharp and adapted to sever the elongate element upon contact. In use, as shown in FIG. 16B, the distal end of the flexible longitudinal fixation element 14 is wrapped around the tensioning tool 80. As described above such movement is used to apply tension to the flexible longitudinal fixation element 14. Once the desired tension has been applied to the fixation element 14, the cutting tool 184 is slidably disposed about the shaft of the tensioning tool 180, such that the flexible longitudinal fixation element 14 is situated within the notch 188 of the cutting tool 184. The cutting tool 184 is rotated counter clockwise to press the sharp edge of the notch against the longitudinal fixation element 14 and cut it. In some embodiments, one side of the notch 188 of the cutting tool 184 is blunt and the other side is sharp. Alternatively, both sides of the notch 188 in the cutting tool 184 could be sharp. The alternative configuration allows rotation of the cutting tool in either direction, relative to the tensioning tool to cut the flexible longitudinal fixation element.

Figure 17C:
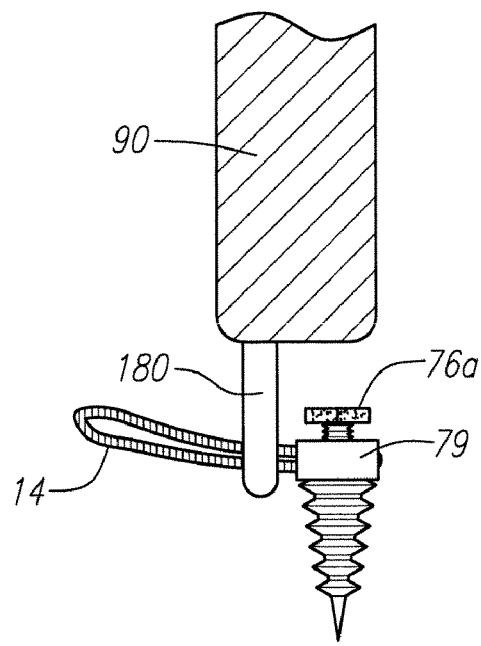
FIG. 17C is a lateral view of the embodiment in FIG. 17A showing the anchor driver partially retracted.
Figure 17D:
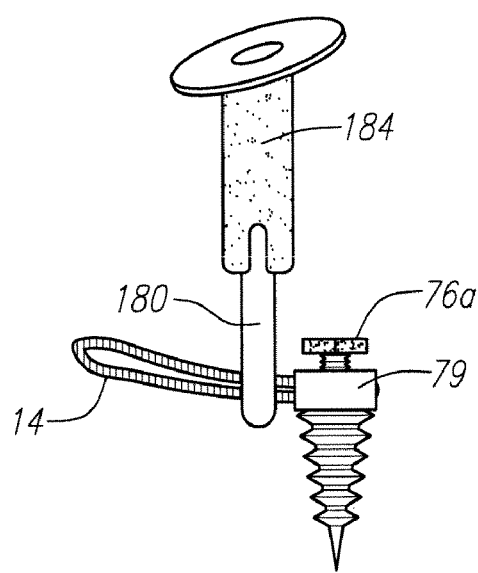
FIG. 17D is a lateral view of the embodiment in FIG. 17C showing a cutting tool partially advanced over the tensioning tool.
Figure 17E:
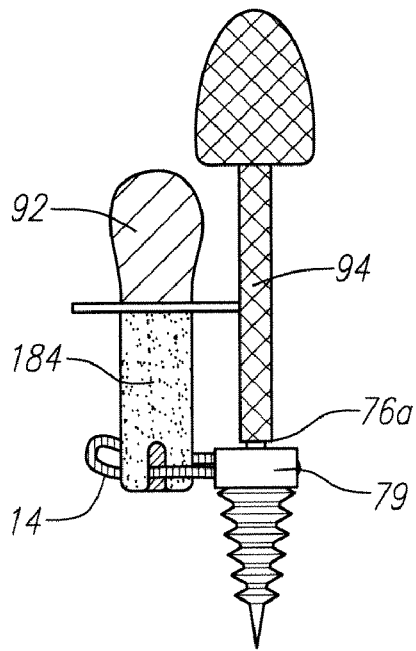
FIG. 17E is a lateral view of the embodiment in FIG. 17D illustrating a removable handle being used with the tensioning tool and a screw driver on anchor.

FIG. 17A is a lateral view of the anchor 79 and tensioning tool 180 drawn in FIG. 15A and the end of an anchor driver 90. Anchor driver 90 is an elongate tubular member, analogous to a screw driver, used to insert the anchors into a vertebra. In use, as shown in FIG. 17B, an anchor 79, pre-threaded with a longitudinal fixation element 14 is located on the distal end of the anchor driver. The shaft of the tensioning tool 180 is slidably inserted in the lumen of the anchor driver 90. Anchor driver 90 is then used to insert anchor 79 into a vertebra using methods commonly know to those skilled in the arts. Once the anchor 79 has been inserted into the vertebra, the tensioning tool 180 is rotated to apply tension to the longitudinal fixation element, as discussed above and shown in FIG. 17C. Once the desired tension has been applied to the longitudinal fixation element 14, the cutting tool, such as cutting tool 184 illustrated in FIG. 16A is advanced over the shaft of the tensioning tool 180. As shown in FIG. E, a screwdriver 94 is inserted into screw 76a to tighten and shear off the head of the screw after the desired tension has been applied to the flexible longitudinal fixation element. Counter rotation may be applied to the anchor 79 as the screw 76a is tightened. The screw 76a, however, is preferably tightened with only the counter rotation applied by the bone and the tensioning tool 180. The cutting tool 184 is rotated using the attached handle 92 to cut the flexible longitudinal fixation element 14 after the screw 76a is tightened.

Figure 19A:
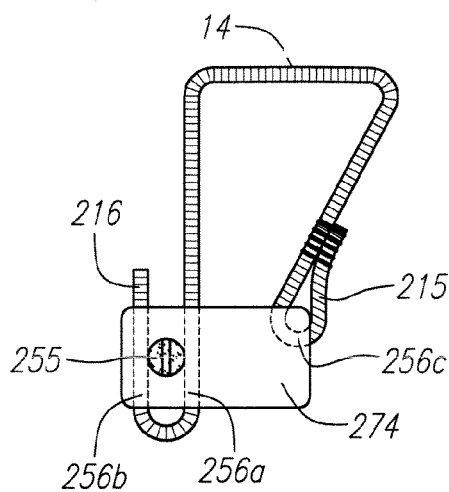
FIG. 19A is a top view of an alternative embodiment of an anchor and longitudinal fixation element.
Figure 19B:
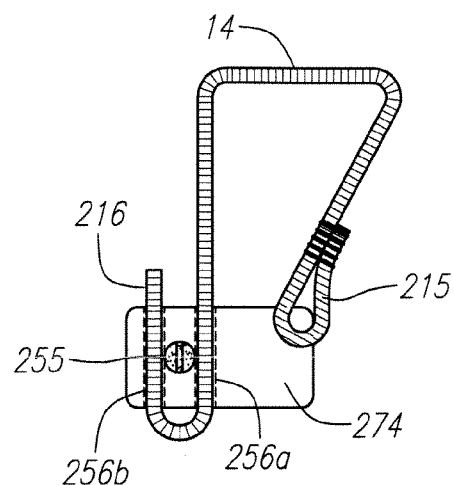
FIG. 19B is a cross-sectional view of the embodiment illustrated in FIG. 19A.
Figure 19C:
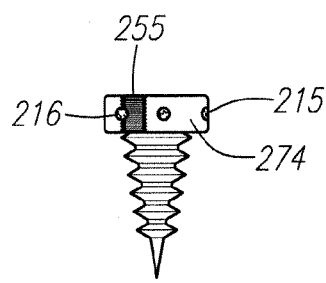
FIG. 19C is a coronal cross-section of the embodiment illustrated in FIGS. 19A-B illustrating the cam component in the open position.
Figure 19D:
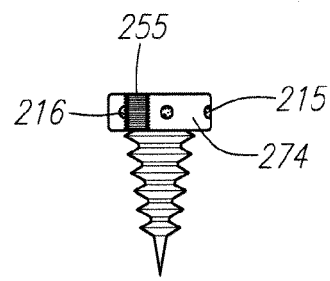
FIG. 19D is a coronal cross-section of the embodiment in FIGS. 19A-B illustrating the cam component in the locked position
Figure 19E:
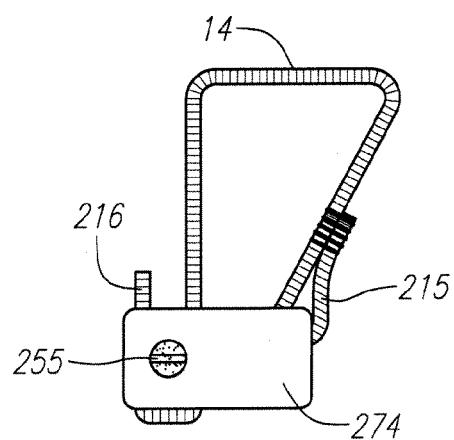
FIG. 19E is a top view of the embodiment in FIGS. 19A-D.

FIGS. 19A-D illustrate an alternative embodiment of a cam-locking anchor 274 preassembled with a longitudinal fixation element 14a,b. The first end 215 of the flexible longitudinal fixation element 14 has been fastened to the anchor 274 using previously described methods. The second end 216 of the flexible longitudinal fixation element 14 was threaded through two passages 256a,b in the anchor 274. A cam lock component 255 is configured to engage the portion of the longitudinal fixation element 14 in the passage 256b in order to fasten the second end 16 of the longitudinal fixation element 14 to the anchor 274. As discussed above, cam lock anchors can advantageously provide an infinite range for tightening longitudinal fixation elements around hooks anchors enabling finer variations on the tension applied to the longitudinal fixation element. As shown in FIG. 19C, the anchor 274 is supplied with the cam lock 255 rotated into an open or unlocked position to permit advancement of the flexible longitudinal fixation element 14 through the passages 256a,b anchor 274. Once the anchor has been positioned in the vertebra and the desired tension has been applied to the longitudinal fixation element 14, the cam lock 255 is rotated into a locked position, as shown in FIGS. 19D-E, to press the longitudinal fixation element between the cam component 255 and the side wall of passage 256b, The configuration fastens the second end 216 of the flexible longitudinal fixation element 14 to the anchor 274 and also enables the anchor to maintain tension on the flexible longitudinal fixation element. As discussed above, the ends 216 of the flexible longitudinal fixation element 14 can be treated to resist wear by the cam component 255.

Figure 19F:
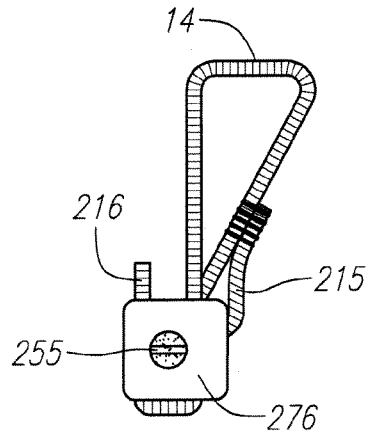
FIG. 19F is a top view of an alternative embodiment of the anchor in FIGS. 19A-E showing the passages stacked vertically to reduce the width of the anchor.
Figure 19G:
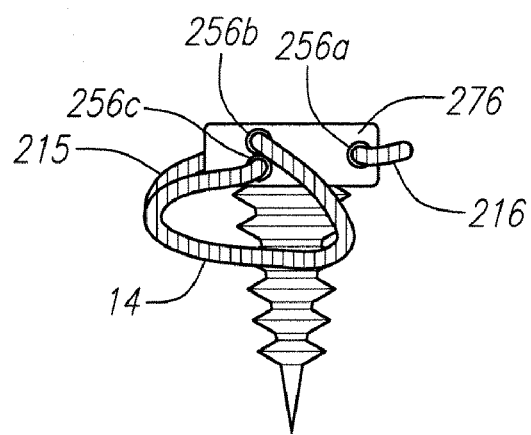
FIG. 19G is a lateral view of the embodiment illustrated in FIG. 19F.

In an alternative embodiment, as shown in FIGS. 19F-G, the passages 256a,b for the second end of the longitudinal fixation element 14 can be stacked vertically to reduce the width of the anchor 276

Figure 20C:
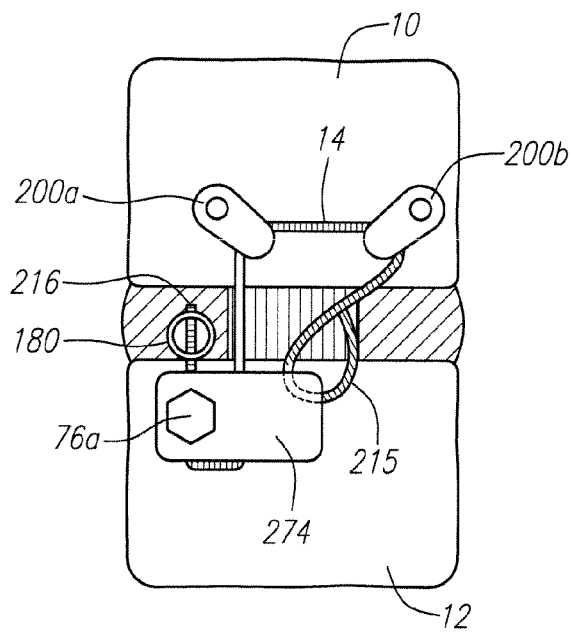
FIG. 20C is an anterior view of a portion of the spine in FIG. 20B illustrating the placement of a second anchor placement tool.

In some embodiments, an anchor placement or locator tool can be used to aid the surgeon in determining the optimum location(s) for one or more anchors of a specific flexible spinal stabilization system relative to one or more anchors that have already been inserted in an adjacent vertebra, thereby minimizing the amount the tensioning tool must be rotated to apply the appropriate tension to the longitudinal fixation element. For example, FIGS. 20A-F illustrate an anchor placement tool 200 for determining the optimum location for hook anchors 3a,b in the adjacent vertebra relative to a specific locking anchor/longitudinal fixation element combination that is used in the adjacent vertebra. FIG. 20A is a lateral view of an anchor placement tool 200 to help surgeons optimize location of the anchors in the vertebrae. The anchor placement tool 200 has a spike like first portion for making a hole in the vertebra where the hook anchor should be inserted and a small hook at the opposite end for temporarily engaging the loop of the longitudinal fixation element. In use, as shown in FIGS. 20B-C, a locking anchor, such as anchor 274, pre-threaded with a longitudinal fixation element 14, is placed in caudal vertebra 12. A first spike-like anchor placement tools 200a is placed over the flexible longitudinal fixation element 14 to determine the optimum location for the first hook anchor and forced into the cranial vertebra 10 to create a hole for the anchor. A removable tool, not shown, may be temporarily fastened to the anchor placement tool 200 to facilitate spike placement. The shaft of the tensioning tool 180 can be seen over the distal end 216 of the flexible longitudinal fixation element 14.

Figure 20D:
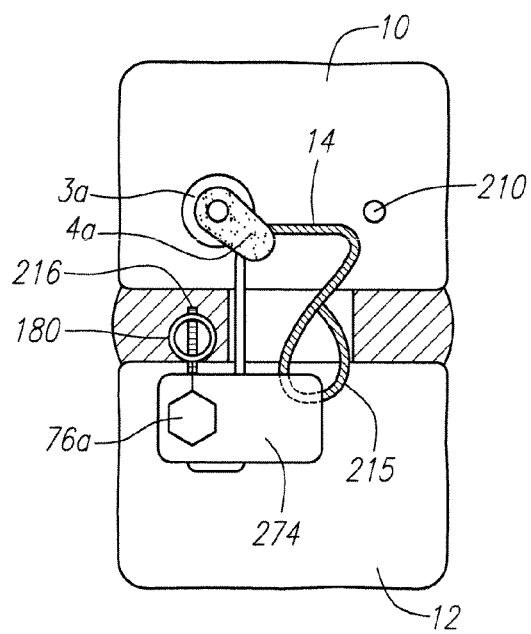
FIG. 20D is an anterior view of a portion of the spine illustrating the second anchor locator tool removed from the cranial vertebrae.
Figure 20E:
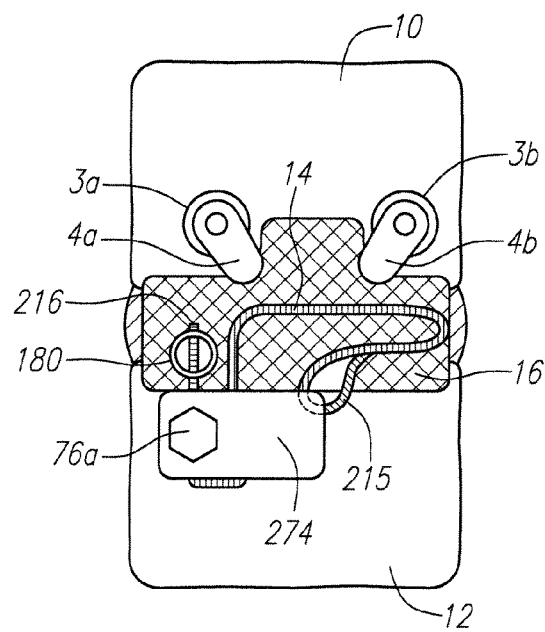
FIG. 20E is an anterior view of a portion of the spine illustrating anchors placed in the holes made by the anchor locator tools.
Figure 20F:
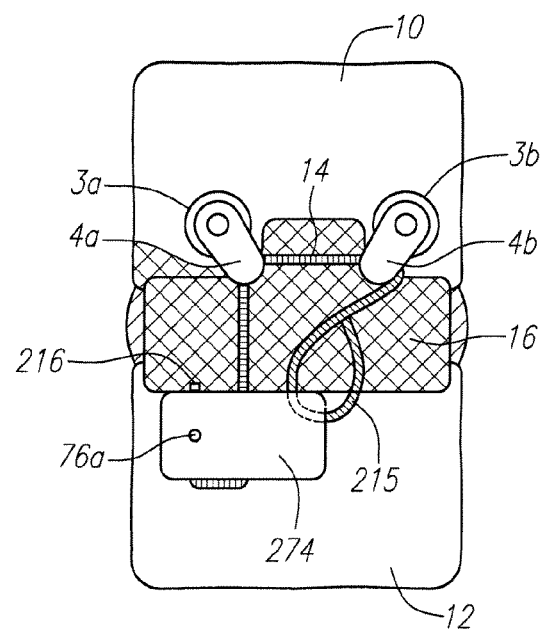
FIG. 20F is an anterior view of a portion of the spine illustrating a flexible longitudinal fixation element placed around anchors placed in the holes made by the anchor locator tools.

Next, as shown in FIGS. 20C-D, a second spike 200b is placed over the longitudinal fixation element 14 to determine the optimum location of the second hook-like anchor and then pressed into the cranial vertebra 10 to make a hole 210 marking the location for the second hook like anchor. Next, as shown in FIG. 20E, hook like anchors 3a,b previously described with respect to FIG. 1A are placed in the holes 210 created by the anchor placement tool 200. As shown in FIG. 20F, the flexible longitudinal fixation element 14 attached to anchor 274 is inserted into hooks 4a,b and tension is applied to the second end of the longitudinal fixation element 14 using the tensioning tool 180. In some embodiments, five to 20 pounds of tension is preferably applied to the flexible longitudinal fixation element. Alternatively, 4, 3, 2, 1 pounds or less tension may be applied to the flexible longitudinal fixation elements. Alternatively, 21, 22, 23, 24, 25, 26, 27, 28, 29, 30, 31 pounds of more of tension may be applied to the flexible longitudinal fixation elements. Regardless, the anchor placement tool 200 minimizes the amount the tensioning tool must be rotated to apply the appropriate tension to the flexible longitudinal fixation element by using the actual longitudinal fixation element 14 as a guide for locating the hook anchors in the cranial vertebra 10.

FIG. 21A illustrates an alternative anchor placement tool 220 for determining the optimum location for one or more locking anchors in a vertebra relative to a pair of hook anchors placed in the adjacent vertebra. The anchor placement tool 220 includes a flexible band 223 having the desired diameter of the flexible longitudinal element attached to the locking anchor that will be placed in the adjacent vertebra. A cannulated device 220 is slidably attached to the flexible band 223. In use, as shown in FIG. 21B, the flexible band 223 of anchor placement tool 220 has been placed around hooks 24a,b of hook anchors 23a,b located in vertebra 11 to determine the optimum location for locking anchors in vertebra 10. Locking anchors 274a,b were previously placed in the caudal vertebra 10 and hook like anchors 23a,b were previously placed in the intermediate vertebra 10 and connected by flexible longitudinal fixation elements 14a,b in the manner taught in FIGS. 1A-B. The flexible band 223 preferably has a diameter that approximates the length of the longitudinal fixation elements attached to the locking anchors to be placed in vertebra 10. The cannulated device 222 is then aligned over the cranial vertebra 10 to determine the optimal location for a first locking anchor in the cranial vertebra 10. A spike, awl, or drill is placed through the cannulated component to create hole 210 in the cranial vertebra 10. Next, as shown in FIG. 21C cannulated portion 222 is moved to the right side of the cranial vertebra to determine the optimal location for a second locking anchor in the cranial vertebra 10. A spike, awl, or drill is placed through the cannulated component to create second hole 210 in the right side of cranial vertebra 10 for a second locking anchor. Once the holes 210 have been made in the cranial vertebra 10, the anchor placement device 220 is removed and a locking anchor, for example cam-locking anchor 274c previously described in reference to FIG. 19A is placed in hole 210 on the left side of the cranial vertebra 10. Flexible longitudinal element 14c is then inserted into hooks 24a,c of hook anchors 23a,b in the intermediate vertebra 11 and tension is applied to the fixation element as previously described. As discussed above by determining the optimal location for the locking anchors in the cranial vertebra 10, the anchor placement tool 220 minimizes the amount the tensioning tool must be rotated after the flexible longitudinal fixation element 14c is placed in the hook anchors 23a,b.

The process is repeated for the hole 210 on the right side of the cranial vertebra 10. Cam locking anchor 274d pre-threaded with longitudinal fixation element 14d is inserted into hole 210. Flexible longitudinal fixation element 14c is then inserted into hook anchors 23a,b and tension is applied to the fixation element 14c. In some embodiments, as shown in FIG. 21E, an anti-adhesion component 230, made of such materials as ePTFE, autograft, allograft, or xenograft tissues, further described in co-pending patent application 60/808, 795, filed May 26, 2006, entitled "Fastening Assemblies for Disc Herniation Repair and Methods of Use," hereby expressly incorporated by reference in its entirety can be placed over most of the flexible fixation system to helps prevent injury to delicate structures such as nerves, blood vessels, and the esophagus from the exposed portions of the anchors. Here, a portion of the anti-adhesion component 230 was placed under the vertical arm of the flexible longitudinal fixation element 14c prior to applying tension. Tension was applied to the end of the flexible longitudinal fixation element 14c and the screw, or cam-loc in anchor 274d was tightened. The vertical arm of the longitudinal fixation element 14c now holds the anti-adhesion patch 230 against vertebrae 10, 11, 12 and the exposed anchors 274a,b,c and 23a,b. As shown in FIG. 21F, flap 231 of the anti-adhesion component 230 is folded over anchor 274d and the exposed portion of longitudinal fixation element 14c.

In an alternative embodiment of a flexible stabilization system, four hook anchors can be used to join adjacent vertebrae 10, 12 using two longitudinal fixation elements 14a,b in a cross-braced arrangement. As, shown in FIG. 22, hook-like anchors 3a-d were placed into the cranial 10 and caudal 12 vertebrae. Two flexible longitudinal fixation elements 14a,b connect the anchors 3a-d. Flexible longitudinal element 14a has been placed around hooks 4a,c,d and flexible longitudinal element 14b has been placed around hooks 4b,c, d. The flexible longitudinal elements 14a,b each are formed into a loose loop prior to insertion by attaching the first and second ends with a cam 306a,b. Once the flexible longitudinal elements 14a,b have been looped around the hook anchors 3a-d, tension is applied to the ends of the flexible longitudinal fixation elements, for example by pulling both ends in opposite directions with a tensioning device, not shown, to capture the longitudinal fixation elements in the hooks 4a-d and apply tension across the anchors 3a-d. In some embodiments, the first and second ends of the fixation elements 14a,b extending through cams 306a,b can have enlarged ends, as previously described with respect to FIGS. 6A-D, for use with a tensioning tool. Once the desired tension has been applied to longitudinal fixation elements 14a,b, cam fasteners 306a,b are rotated into a locked position to maintain tension on the flexible longitudinal fixation elements 14a,b. Alternatively, as shown in FIG. 23 the ends of the flexible longitudinal fixation elements 14a,b can be formed into the loop configuration by attaching the first and second ends to cable tie-like straps 341a-d. As described previously with respect to FIGS. 3A-B, the cable tie straps 341a-d each have a plurality of horizontally extending ribs configured to engage a ratchet mechanism in the cable tie component 340a,b which prevents the cable tie straps 340a-d from sliding backwards in cable tie components 340a-b once it has been pulled there through. Here, cable tie straps 341a-d can be pulled trough the cable tie components to tighten the longitudinal fixation elements 14a,b around hooks 4a-d and apply tension across the vertebrae 11, 12.

Figure 24:
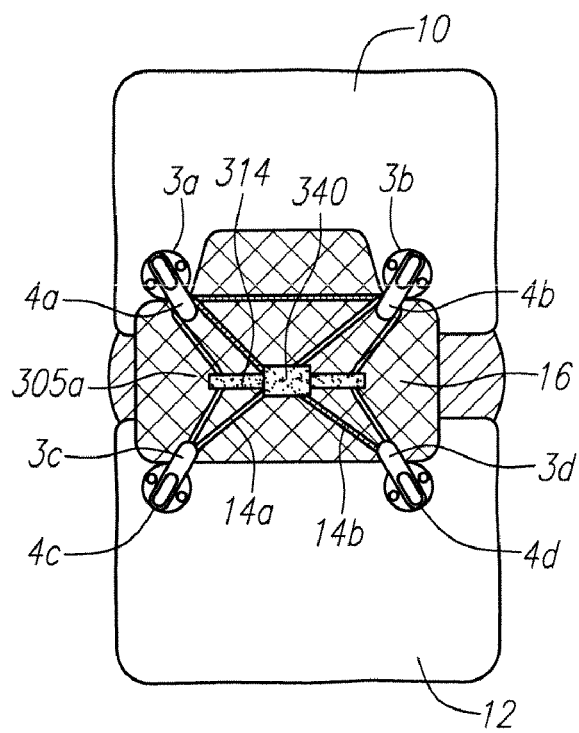
FIG. 24 is an anterior view of a portion of the spine illustrating an alternative embodiment of a flexible fixation system using four hook anchors in the cranial and caudal vertebrae.

In some embodiments, as shown in FIG. 24, a transverse component 314 is fastened around the vertical portions of the flexible longitudinal fixation components 14a,b after they have been captured in hook anchors 4a-d. In use, the transverse component 314 is wrapped around the vertical arms of the longitudinal fixation element, tension is applied to the ends of the transverse component 314 and they are joined together, for example by crimping or alternatively using any of the cam or cable tie components previously described herein. Here, shortening the transverse component with a cable tie component 340 applies tension to the flexible longitudinal fixation components 14a,b The transverse component 314 can be used to apply additional tension to the flexible stabilization systems illustrated in FIGS. 22-23. Alternatively, the transverse component 314 can be used instead of the cam or cable tie components described in FIGS. 22-23 to provide tension across longitudinal fixation elements having a fixed diameter.

Figure 26A:
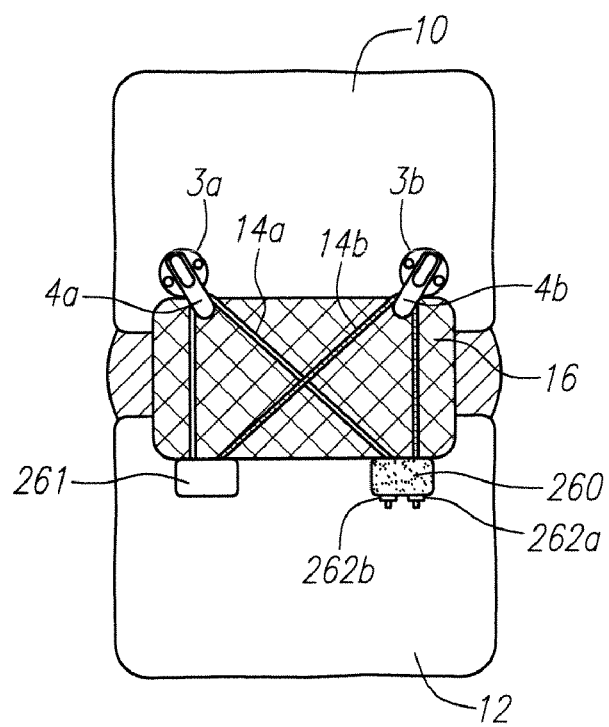
FIG. 26A is an anterior view of a portion of the spine illustrating an alternative embodiment of a flexible fixation system.
Figure 26B:
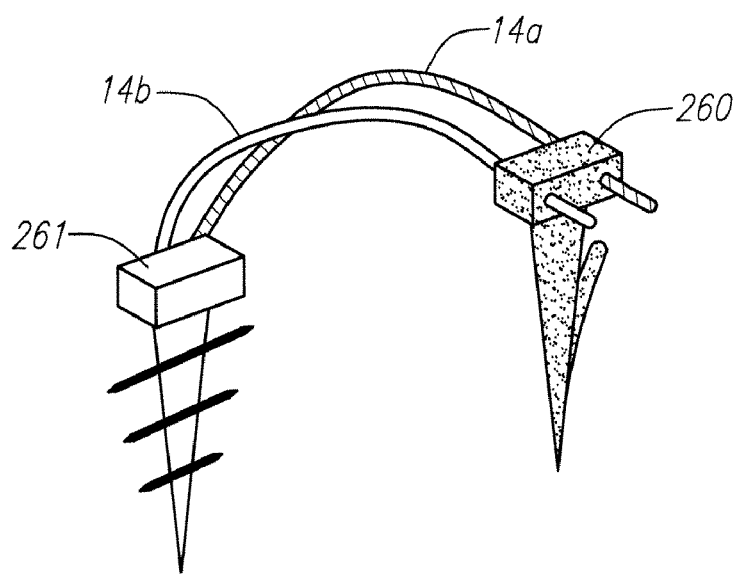
FIG. 26B is an oblique view of two of the anchors and attached flexible longitudinal fixation elements shown in FIG. 26A.

FIG. 26A-B illustrate an alternative embodiment of a flexible stabilization system for joining two adjacent vertebrae The first ends of two flexible longitudinal fixation elements 14a,b are fastened to a screw type anchor 261 prior to insertion, shown here in the right side of the caudal vertebra 12. The second ends are likewise threaded through passages in a push in type anchor 260 prior to insertion of the anchors in the vertebrae. In use, screw in anchor 261 is screwed into the right side of the caudal vertebra 12 with the first ends of the flexible longitudinal fixation elements 14a,b extending there from. Since push-in anchor 260 does not need to be rotated to be inserted into the vertebra, it can also be pre-threaded with the second ends of the longitudinal fixation elements 14a,b. As shown in FIG. 26a, push in anchor 260 is inserted into the left side of the caudal vertebral pre-threaded with the second ends of the longitudinal fixation elements. The flexible longitudinal fixation elements 14a,b are then passed through hook-like anchors 3a,b in the cranial vertebra 10 and tension is applied to the second ends of the flexible longitudinal fixation elements extending through the push in anchor 260. Once the desired amount of tension has been applied, the second ends of the flexible components 14a,b are fastened to the "push in" anchor 260 using any of the methods previously described herein or known in the art. For example, as shown in FIG. 26A crimps 262a,b may be placed over the second ends of the flexible longitudinal fixation components 14a,b to maintain tension on the fixation elements 14a,b. This embodiment, like the other embodiments described in this application, enables the ends of the flexible longitudinal fixation elements 14a,b to be passed through passages in the both anchors 260, 261 before the anchors 260, 261 are placed in the vertebrae. Such configuration eliminates the need for surgeons to pass flexible longitudinal fixation elements through small holes deep within a surgical wound.

Figure 27A:
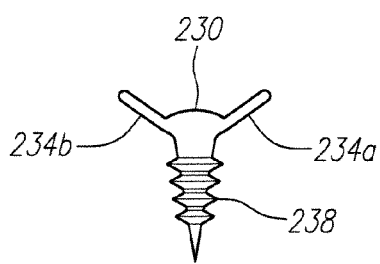
FIG. 27A is a lateral view of an alternative embodiment of a hook anchor.
Figure 27B:
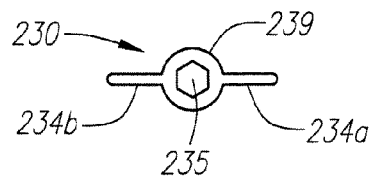
FIG. 27B is a top view of the anchor illustrated in FIG. 27A.
Figure 27C:
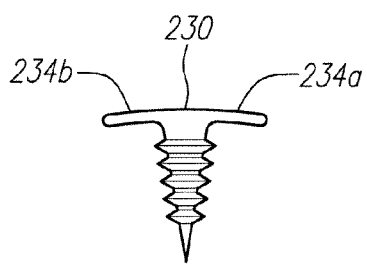
FIG. 27C is a lateral view of the anchor illustrated in FIG. 27A.
Figure 27D:
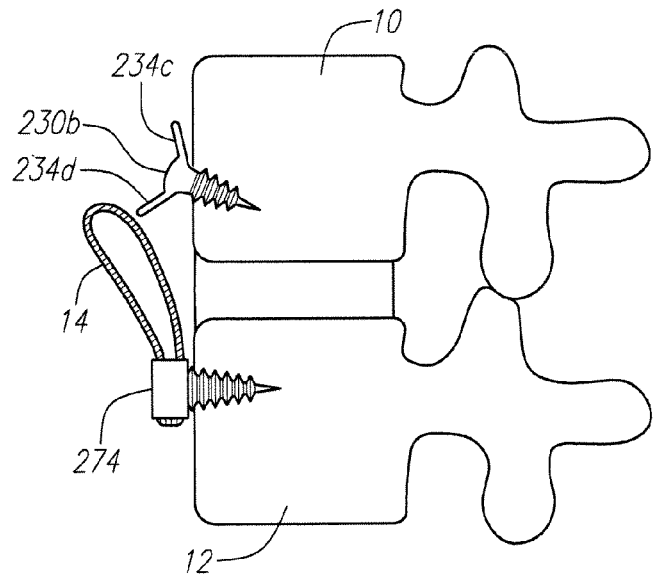
FIG. 27D is a lateral view of a partial sagittal cross-section of the spine illustrating use of the anchor shown in FIG. 27A in the cranial vertebrae.
Figure 27E:
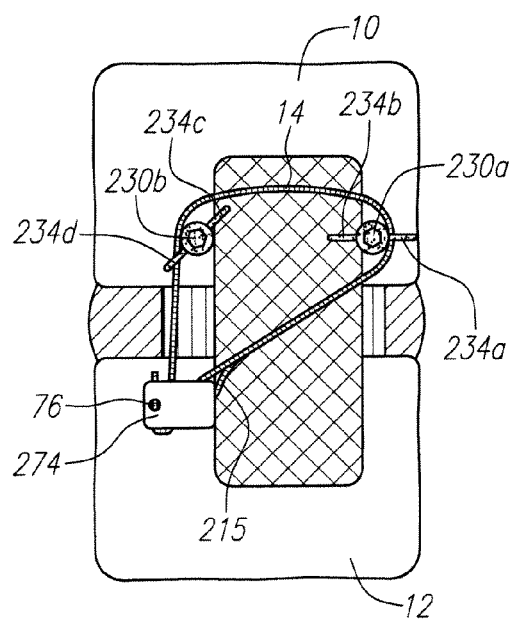
FIG. 27E is an anterior view of a portion of the spine and the embodiment shown in FIG. 27D.
Figure 27F:
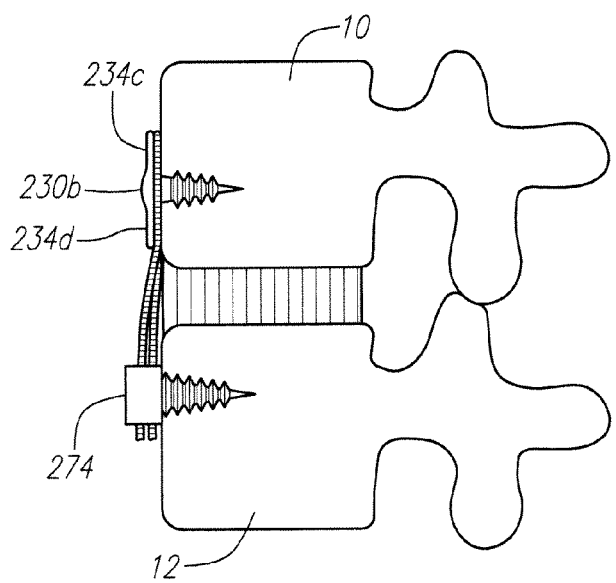
FIG. 27F is a lateral view of a partial sagittal cross-section of the embodiment shown in FIG. 27D showing the arms of the anchor forced into a second position in the cranial vertebrae.
Figure 27G:
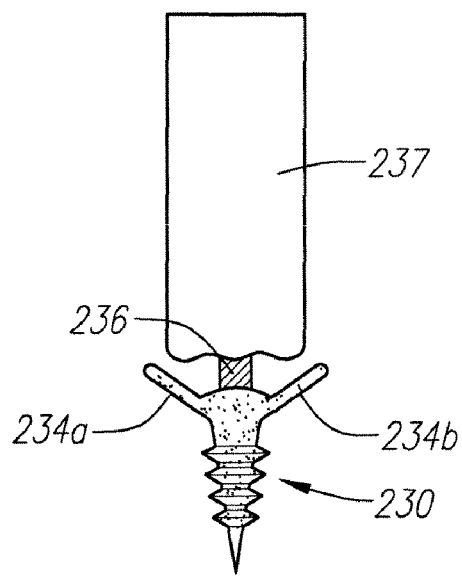
FIG. 27G is a lateral view of the anchor in FIG. 27A and a tool for forcing the arms of the anchor into a second position.
Figure 27H:
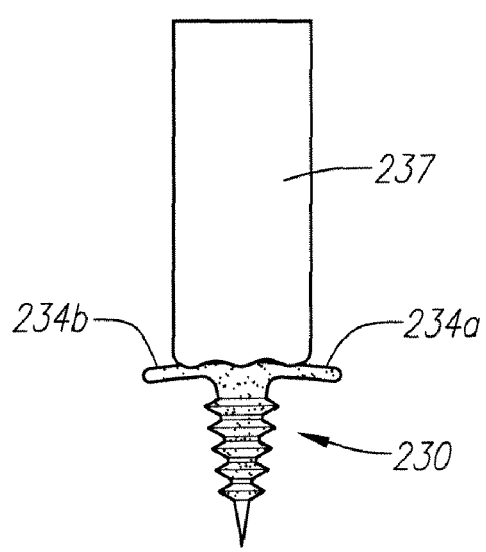
FIG. 27H is a lateral view of the embodiment in FIG. 27G showing the arms of the anchor forced into the second position.

In some embodiments an alternative hook-like anchor 230 can be used with the flexible stabilization systems described herein. As shown in FIGS. 27A-C, hook-like anchor 230 has two arms 234a,b extending from the head 239 of the anchor 230. Anchors 230 are initially provided with arms 234a,b extending from the head 235 at an angle as shown in FIG. 27A. As shown in FIG. 27D, this position facilitates insertion of the anchor 230 into the vertebrae at angles other than ninety degrees. Once the anchors 230 have been inserted into the spine and one or more longitudinal fixation elements have been looped around the arms 234a,b, the arms 234 are forced into a second position, extending perpendicular from the screw portion 238 of the anchor 230 in order to trap the fixation elements between the vertebra and the arms 234a,b of the anchor 230. In some embodiments, as shown in FIGS. 27G-H, a tool 237 can be used to force the arms 234a,b of the anchor 230 from the first position to a second position. Here, the inner component 236 of the tool 237 is placed into a recess 235 in the head 239 of the anchor 230. For example, the inner component 236 of the tool 237 can be placed into a hexagon recess 235 in the top of the anchor 230. The outer sleeve of the tool 237 is then impacted into the arms 234a,b of the anchor 230. The tool 237 forces the arms 234a,b of the anchor 230 into a second position. The recesses in the tip of the tool 237 are sized to fit the arms of the anchor. Alternatively, the anchor 230 could be made of shape memory material. For example, the arms 234a,b of anchors 230 made of shape memory materials could change position as the temperature of the anchor 230 changes.

The hook-like anchors 230 can be used in combination with any of the locking anchors and flexible longitudinal fixation elements described herein to provide a flexible stabilization system for joining two or more vertebra in a cross-braced arrangement. In one embodiment, as shown in FIGS. 27D-F, hook-like anchors 230a,b are placed in cranial vertebra 10 and locking anchor 274 is placed in caudal vertebra 12. A loop of the longitudinal fixation element 14, attached to locking anchor 274, is placed around anchors 230a,b. As shown in FIG. 27D, the arms 234c,d of the anchor 230 are in the first position to facilitate placement of the fixation element 14 around the anchor 230. Tension is then applied to the end of longitudinal fixation element 14 extending from anchor 274 using any of the tools or methods previously described herein. Once the desired tension has been applied to the fixation element 14, the arms 234a-d of anchors 230a,b are forced into the second position, as shown in FIG. 27F, to hold the flexible longitudinal fixation element 14 under the anchors 230a,b. The second position of the arms 234a-d of the anchors 230a,b also lowers the profile of the anchors 230a,b.

Figure 28A:
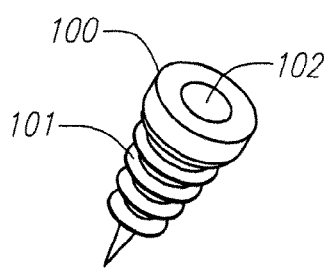
FIG. 28A is an oblique view of the screw portion of an alternative embodiment of an anchor.
Figure 28B:
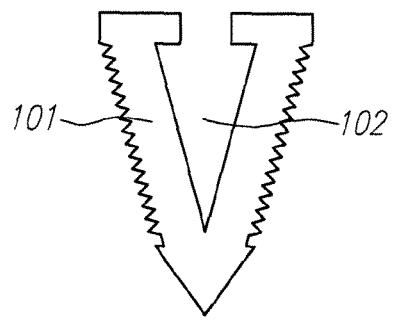
FIG. 28B is a saggital cross-section of the screw portion shown in FIG. 28A.

FIG. 28A-B illustrates an alternative embodiment of an anchor component for use with detachable eyelet and locking components to provide a flexible stabilization system for two or more vertebrae. Anchor component 100 has a screw portion 101, i.e., a first portion adapted for insertion into a bone, e.g., vertebrae. Anchor component 100 also has a cavity 102 that extends through at least part of the screw portion 101. Detachable components such as locking component 103 or eyelet component 109 can be inserted into cavity 102 to provide eyelet and locking anchors.

Figure 28C:
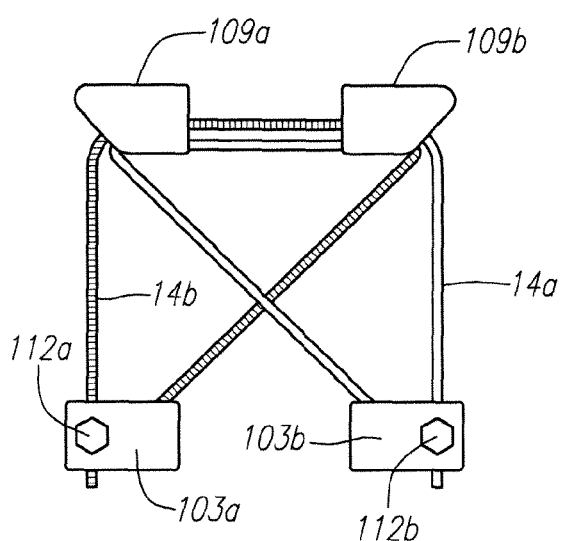
FIG. 28C is a top view of an alternative embodiment of a flexible spinal stabilization system.
Figure 28D:
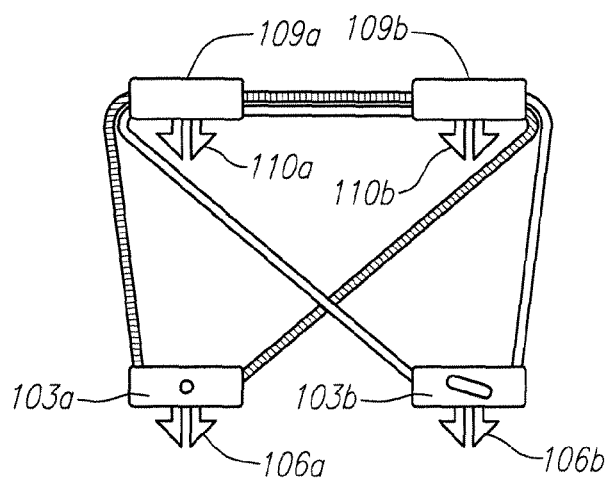
FIG. 28D is an oblique view of the embodiment illustrated in FIG. 28C.
Figure 28E:
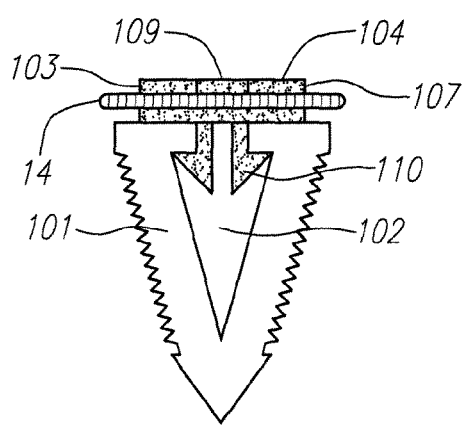
FIG. 28E is a sagittal cross-section of anchor comprising a screw portion and a detachable, eyelet component for use with the embodiment illustrated in FIGS. 28C-D.

The eyelet anchor, illustrated in FIG. 28E, comprises an eyelet component 109 attached to an anchor component 100 by inserting the deformable projection 106 into the cavity 102 of the anchor component 100. The eyelet component 109 has one or more passages 107 extending along an axis perpendicular to a longitudinal axis of the screw portion 100 adapted to receive at least one elongate element 14 there through. In one embodiment, the detachable component 10-9 has a single passage 107 configured to hold two fixation elements 14a,b. Alternatively, detachable components 109 can have first and second passages, each configured to house a single fixation element.

Figure 28F:
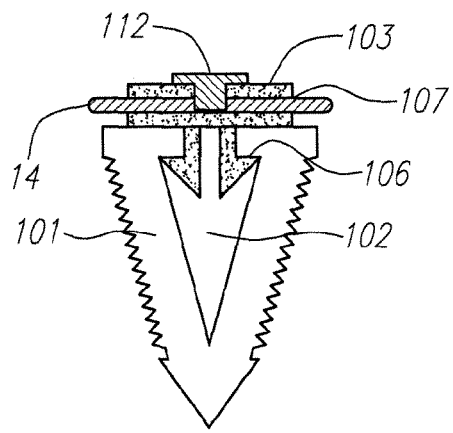
FIG. 28F is a sagittal cross-section of anchor comprising a screw portion and a detachable, locking component for use with the embodiment illustrated in FIGS. 28C-D.

The locking anchor, illustrated in FIG. 28F, comprises a locking component 103 attached to an anchor component 100 by inserting the deformable projection 106 into the cavity 102 of the anchor component 100. The locking component 103 have an enlarged head 104 having at least one passage 107 extending along an axis perpendicular to a longitudinal axis of the screw portion 100 which is adapted to slidably receive the second end of at least one fixation element 14. A threaded bore 108 extends perpendicular to the passage 107 and communicates with the passage 107. A screw 112 is inserted into the threaded bore 108. In use, the screw 112 can be advanced through the threaded bore 108 and into passage 107 to engage fixation element 14 threaded through passage 107 and hold the fixation element 14 in place against a side wall of passage 107. A first end of the fixation element 14 is attached to the enlarged head 104 using any of the methods previously described.

As shown in FIGS. 28D-F, eyelet components 109a,b and locking components 103 have deformable components 106a,b and 110a,b projecting from the bottom side of the components 103, 109 along an axis that is generally perpendicular to passages 107. The deformable components 106a,b 110a,b sized for insertion into the cavity 102 of the anchor component 100 and adapted to bear against a portion of the cavity 102 such that the detachable components 109, 103 and the anchor components 100 are locked together, to form eyelet and locking anchors shown in FIGS. 28E-F for use in a flexible stabilization system.

The anchor components 100 and detachable eyelet 109 and locking 103 components are preferably made of titanium or other MRI compatible material. Alternatively, the components could be made of plastic such as Delron, or a bioresorbable such as polylactic acid (PLA), polyglycolic acid (PGA), poly (ortho esters), poly(glycolide-co-trimethylene carbonate), poly-L-lactide-co-6-caprolactone, polyanhydrides, poly-n-dioxanone, poly(PHB-hydroxyvaleric acid), or combinations thereof.

The framework for the stabilization system can be pre-assembled independently of the anchor components. For example, in one embodiment for joining two vertebra, shown in FIGS. 28C-D, the first ends of flexible longitudinal fixation elements 14a,b are attached to locking components 103a,b. The second ends of the fixation elements 14a,b are then threaded through passages in two eyelet anchor components 109a,b and through a passage in one of the locking anchor components 103a,b to create a cross braced arrangement for a stabilization device. Since the anchor components 100 can be screwed into the vertebra prior to attaching the detachable eyelet and locking components, the flexible longitudinal fixation elements 14a,b can be threaded through the eyelet components 109a,b and locking components 103a,b to create the desired crossed-braced arrangement prior to insertion in the spine, thus eliminating the need for the surgeon to try to thread the fixation elements through the anchors deep within the would site. Once the eyelet and locking components 103a,b and 109a,b have been snapped into the anchor components placed in the vertebrae, tension can be applied to the second ends of the longitudinal fixation elements 14a,b and screws 112a,b can be tightened to maintain the tension across the vertebrae.

Figure 29A:
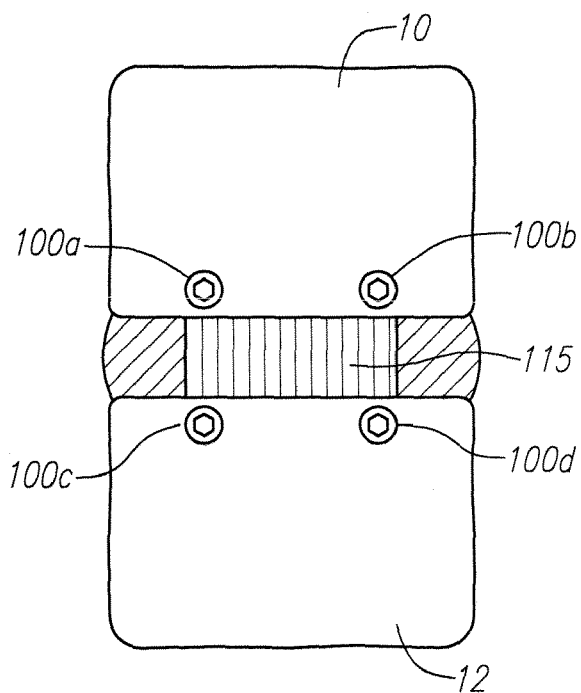
FIG. 29A is an anterior view of a portion of the spine illustrating placement of the screw portions shown in FIG. 28A in the vertebrae.
Figure 29B:
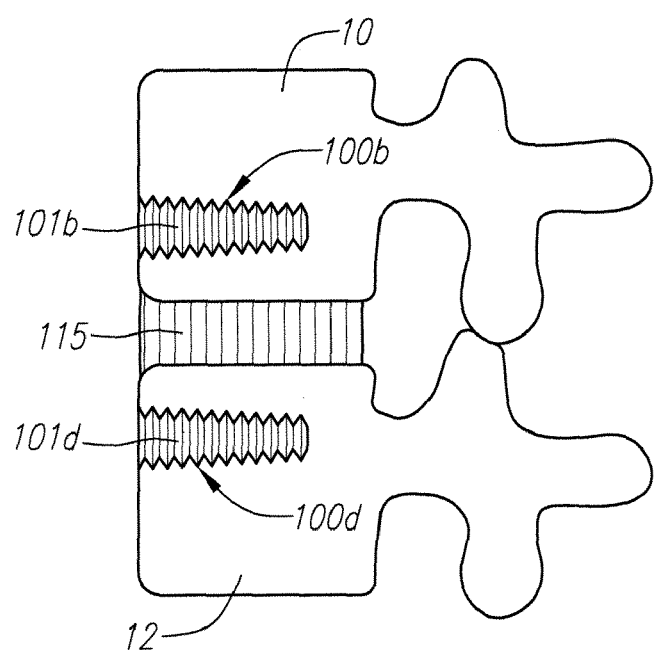
FIG. 29B is a partial sagittal view of the embodiment shown in FIG. 29A.
Figure 29C:
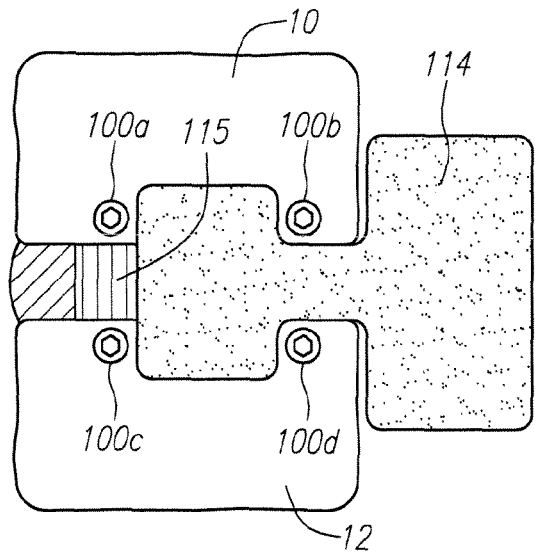
FIG. 29C is an anterior view of the embodiment in FIG. 29A illustrating an anti-adhesion component placed against the spine.

In use, as shown in FIGS. 29A-E, an intradiscal device 115, such as an interbody cage, is inserted into the disc between vertebrae 10, 12. Two anchor components 100a,b are inserted into the cranial vertebra 10 and two anchor components 100c,d are inserted into the caudal vertebra 12. In some embodiments, an anti-adhesion component will be used to cover the longitudinal fixation elements and anchors as described in co-pending patent application 60/808,795, filed May 26, 2006, entitled "Fastening Assemblies for Disc Herniation Repair and Methods of Use," hereby expressly incorporated by reference in its entirety. For example, as shown in FIG. 29C the mesh 112 of a composite mesh anti-adhesion component 114, illustrated in FIG. 29F, is placed against vertebrae 10, 12 between anchors components 100a-d such that the mesh component 112 lies adjacent and at least partially covers the intradiscal device 115 and the anti-adhesion flap 116 is facing outwardly.

Figure 29D:
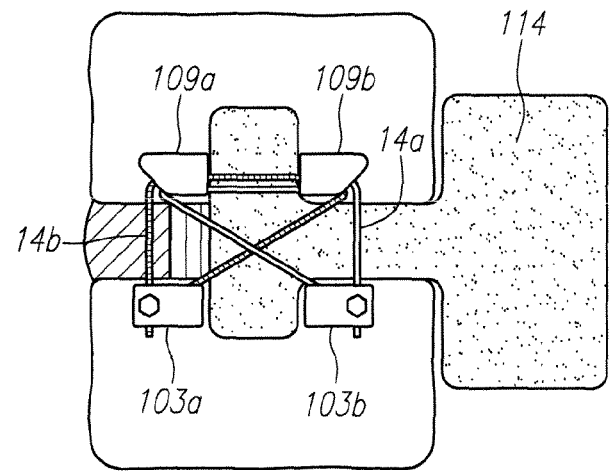
FIG. 29D is an anterior view of the embodiment in FIG. 29C illustrating the flexible spinal stabilization system shown in FIGS. 28C-F placed in the screws previously inserted into the vertebrae.

Next, as shown in FIG. 29D, the deformable projections 106a,b and 110a,b of the eyelet and locking components 103a,b and 109a,b preassembled with flexible longitudinal fixation elements 14a,b in a loose configuration as shown in FIGS. 28C-D are snapped into the anchor components 100a-d to create a stabilization system joining vertebrae 10, 12. In alternative embodiments, other mechanisms may be used to fasten the anchor components 100a-d and the eyelet 109a,b and locking 103a,b components. For example, in one embodiment, the anchor components and/or the eyelet 109a,b and locking 103a,b components could be made of nitinol and could be fastened with shape memory technology.

Figure 29E:
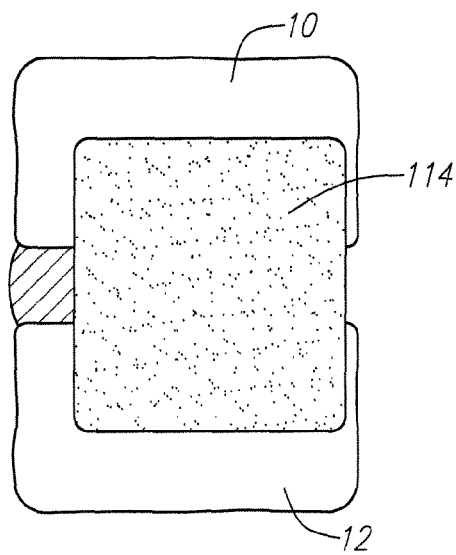
FIG. 29E is an anterior view of the embodiment in FIG. 29D illustrating the anti-adhesion component folded over the flexible spinal stabilization system.
Figure 29F:
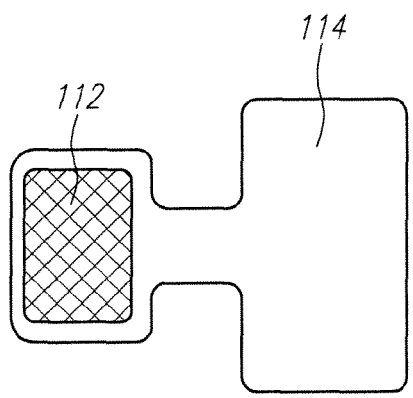
FIG. 29F illustrates an alternative anti-adhesion component.

Once the eyelet 109a,b and locking 103a,b components have been fastened to the previously placed anchor components 100a-d, the second ends of the longitudinal fixation elements 14a,b can be tensioned using any of the methods previously described herein. After the appropriate tension has been applied to the fixation elements, screws 112a,b are tightened to hold the fixation elements 14a,b in place within the locking components 103a,b and maintain tension on the system. The ends of the fixation elements 14a,b are cut off and removed. Next, as shown in FIG. 29E, the anti-adhesion component 114 is folded over the flexible longitudinal fixation elements 14a,b and eyelet 109a,b and locking 103a,b components to help prevent injury to delicate structures such as nerves, blood vessels, and the esophagus from the exposed portions of the anchors.

Figure 30:
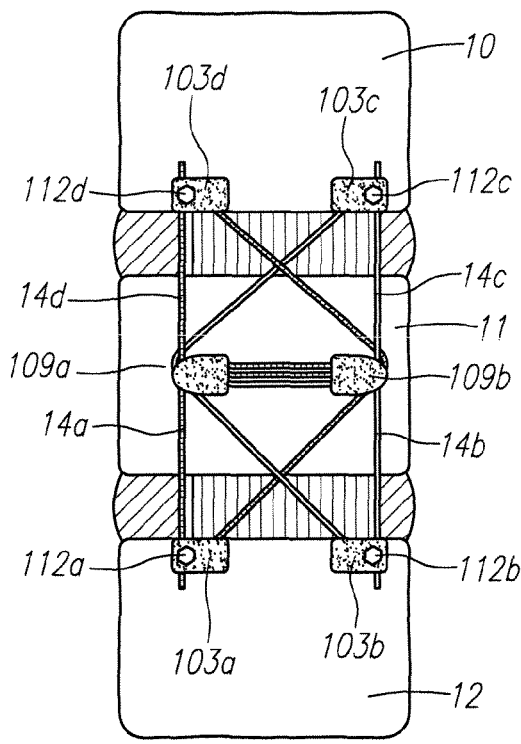
FIG. 30 is an anterior view of a portion of the spine illustrating an alternative embodiment of a flexible spinal stabilization system for a two level system.

In some embodiments, as shown in FIG. 30, and the anchor components 100 and detachable eyelet 109 and locking 109 components can be configured to provide a two-level stabilization device. Similar to FIGS. 29A-F, anchor components 100a-f (not shown) have been inserted into vertebrae 10, 11, 12. Flexible fixation elements 14a,b have been attached to locking components 103a,b inserted into caudal vertebra 12 and threaded through eyelet components 109a,b inserted into middle vertebra 11. Flexible fixation elements 14c,d have been attached to locking components 103c,d inserted into cranial vertebra 10 and threaded through eyelet components 109a,b inserted into middle vertebra 11. Eyelet components 109a,b inserted into the middle vertebra 11 preferably include a passage there through that is adapted to receive an elongate element, alternatively two elongate elements, alternatively three elongate elements, alternatively four elongate elements. Eyelet components 109a,b may alternatively have one passage adapted to receive four elongate elements there through, two passages adapted to receive two elongate elements there through, or four passages adapted to receive one elongate element there through.

As discussed above, the eyelet 109a,b and locking 103a-d components can be assembled with the flexible fixation elements 14a-d prior to insertion into the spine. Once the eyelet 109a,b and locking 103a-d components have been fastened to the previously placed anchor components 100a-f, the second ends of the longitudinal fixation elements 14a-d can be tensioned using any of the methods previously described herein. After the appropriate tension has been applied to the fixation elements, screws 112a-d are tightened to hold the fixation elements 14a-d in place within the locking components 103a,b and maintain tension across vertebrae 10,11,12.

Figure 31A:
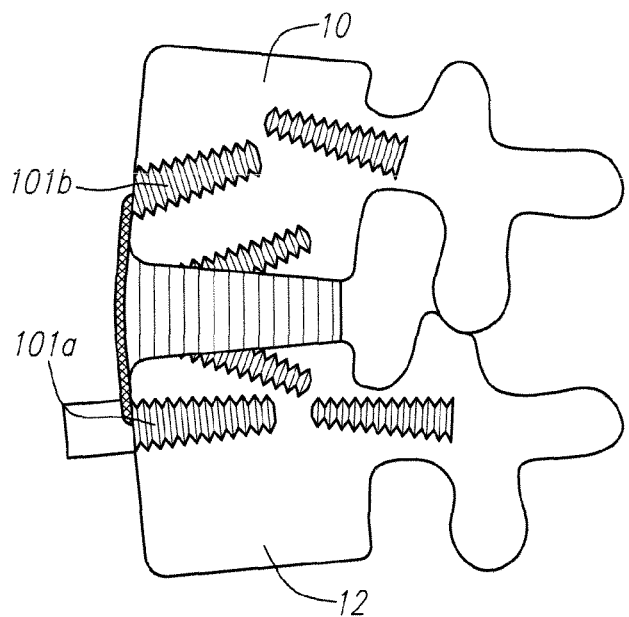
FIG. 31A is a partial sagittal cross-section of a portion of the spine illustrating an alternative embodiment of a flexible spinal stabilization system.
Figure 31B:
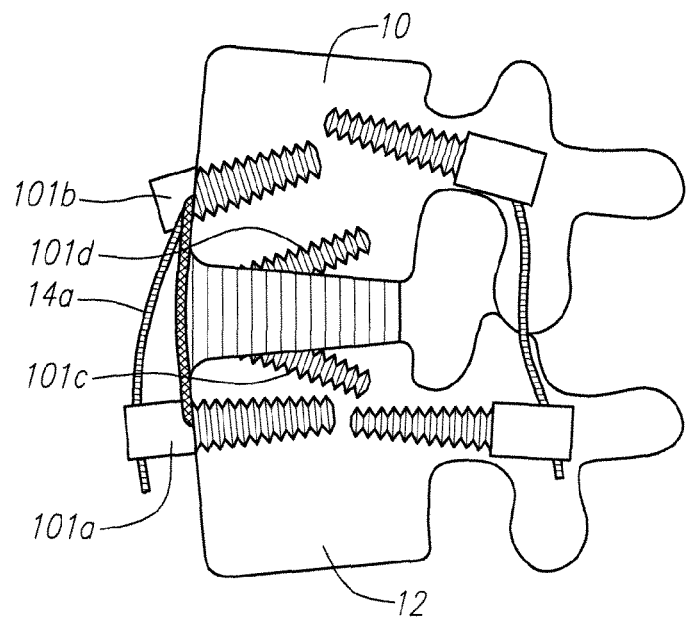
FIG. 31B is a partial sagittal cross-section of a portion of the lumbar spine illustrating an alternative embodiment of a flexible spinal stabilization system.

In some embodiments, as shown in FIGS. 31A-B, the anchors for the stabilization system, such as anchor components 100 can have different length to cause the flexible fixation elements to diverge from the vertebra as they course in a caudal or cranial direction. In FIG. 31A, a mesh component 116 has been fastened to the anterior portion of the interbody cage 115. Anchor components 101a,b were passed through the cage 115 and into the vertebra cranial 10 and caudal 12 to the cage. Here, an alternative embodiment of the anchor components 101a,b illustrated in FIG. 29B were inserted into the vertebrae, however, any of the previously described anchors having different lengths could be used to accomplish the same objective of causing the flexible fixation element to diverge. The anchor component 101a in the caudal vertebra 12 are longer than the anchor components 101b s in the cranial vertebra 10 so that when the locking and eyelet components containing flexible fixation element 14a are snapped into the anchor components 101a,b, the flexible fixation element 14a will diverge from the spine as it courses in the caudal direction. Alternatively, the anchors in the cranial vertebra 10 may be longer than the anchors in the caudal vertebra to cause the flexible fixation element to diverge in a cranial direction. is embodiment increases the stiffness of the instrumented spine compared to a stabilization system comprised of non-diverging flexible longitudinal fixation elements, The flexible stabilization systems described herein can also be applied to the posterior-lateral portion of the spine. For example as shown in FIGS. 32A-C, suture anchors 503a,b were placed in the vertebra caudal 12 to the disc 20. Suture anchors 503a,b suitable for use include any of the hook anchors previously described herein or a standard eyelet anchor described in more detail in co-pending application Ser. No. 11/945,994, entitled "Methods of Anterior Fixation and Stabilization of a Spinal Segment," filed on Nov. 27, 2007, and hereby incorporated by reference in its entirety. Suture anchors 502a,b were placed in the cranial vertebra 10. The anchors 502a,b are preferably "push in" anchors with an expandable or deployable component. Push-in anchors have appendages that expand away from the shaft of the anchor after the anchor is inserted into bone. Alternatively, push in anchors may expand in a radial direction after the anchors are inserted into bone. Push in anchors do not have threads and are not screwed into bone. Push in anchors are generally impacted into bone or holes drilled into bone. Examples of nonscrew-in or push-in anchors include Impact, UltraFix RC, Ultrafix MiniMite anchors (Conmed, Largo Fla.), Bioknotless, GII, Versalok, Micro, and Super anchors (DePuy Mitek), (Raynham Mass.), Bio-SutureTak (Arthrex Naples, Fla.), and Collared Harpoon and Umbrella Cancellous Harpoon (Arthrotek, Warsaw, Ind.). Alternatively, as noted in U.S. application Ser. No. 11/635,829 entitled "Sutures for use in the Repair of Defects in the Anulus Fibrosus," which is hereby expressly incorporated by reference in its entirety, an in-situ curing material, such as a bioactive cement, may be injected into the bone proximal to the anchor to increase the force required to pull the anchor out of the bone. The anchors are preferably about 5 to about 6.5 mm in diameter and about 7 to about 15 mm in length. Alternatively, the anchors may be about 3, about 4, about 7, or about 8 or more millimeters in diameter and about 4, about 5, about 6, about 16, about 17, or about 18 or more millimeters in length.

Anchor 502a has two flexible longitudinal fixation elements 314a,b associated with it. Anchor 502b has one flexible fixation element 314c associated with it. As discussed above, the flexible fixation elements 314a-c can be pre-threaded through a locking mechanism on the push in anchors 502a,b prior to insertion in the spine. In some embodiments, the flexible fixation elements 314a-c can also be threaded through the eyelet of a suture anchors 503a,b prior to insertion in the spine. In such embodiments, the eyelet anchors are preferably push-in type anchors as well to in order to avoid issues associated with rotating a prethreaded system of anchors. After threading the first end of the fixation element 314 through the eyelet, the fixation element can be attached to the suture anchor by any suitable method known in the art such as a knot or crimping. In an alternative embodiment, where anchors 503a,b are hook-like anchors, the fixation elements 314a-c can be engaged by the anchors 503a,b after the anchors 503a,b and fixation elements 314a-c have been inserted into the spine as described in more detain in reference to FIGS. 1A-B. Once the anchors 503a,b and 502a,b and attached fixation elements 314a-c have been inserted into the vertebra 10,12, tension is applied to the flexible longitudinal fixation elements 314a-c to restrict spinal motion.

A mesh component (not shown) may be applied under the flexible longitudinal fixation elements 314a-c. For example, polyester mesh with approximately 1 by 1 mm pores could be placed below the flexible longitudinal elements 314a-c. The mesh is preferably about 0.5 to about 5 mm thick. The mesh may be folded to increase its thickness. For example, the mesh could be folded two to eight times to create a folded component 4 mm thick.

The flexible longitudinal fixation elements 314a-c are preferably multifilament polyester sutures with a breakage strength of about 25 to about 100 or more pounds. Alternatively, the flexible longitudinal elements may be made of resorbable material. As taught in co-pending U.S. application Ser. No. 11/635,829, entitled "Sutures for use in the Repair of Defects in the Anulus Fibrosus," hereby incorporated by reference in its entirety, an in-situ curing material, such as polymethylmethacrylate (PMMA) or a bioactive cement could be injected into the bone proximal to the anchor to increase the pullout resistance of the anchor. The in-situ curing material could also flow into or around the anchor to increase the force required to pull the flexible longitudinal element out of the anchor. For example, the in-situ curing material could surround a suture fastening mechanism within the anchor. Cured material would prevent movement or deformation of the suture fastening components.

For stabilizing the posterior lateral portion of the spine, flexible fixation systems are preferably applied to both posterior lateral corners of the vertebral bodies. Therefore, as shown in FIG. 32B anchors 303c,d, anchors 502c,d, and flexible longitudinal fixation elements 314d-f are applied on the opposite side of the vertebrae 10,12 in the same manner as described above. The systems on both sides of the vertebra are preferably applied endoscopically. The anterior-most flexible longitudinal elements, 314a,f restrict lateral bending of the spine. The flexible element on the left side of the spine tightens to restrict bending the spine to the right. The posterior-most flexible elements 314c,d restrict spinal flexion. The diagonal flexible elements 314b,e limit axial rotation or torsion of the spine and anterior translation of the cranial vertebra. In some embodiments, the posterior-lateral stabilization system described herein may be used with intradiscal devices, such as fusion cages, to restrict spinal motion and facilitate spinal fusion. For example, as shown in FIG. 32C, two spinal cages 105a,b, have been placed in the intradiscal space between vertebrae 10,12.

Figure 33B:
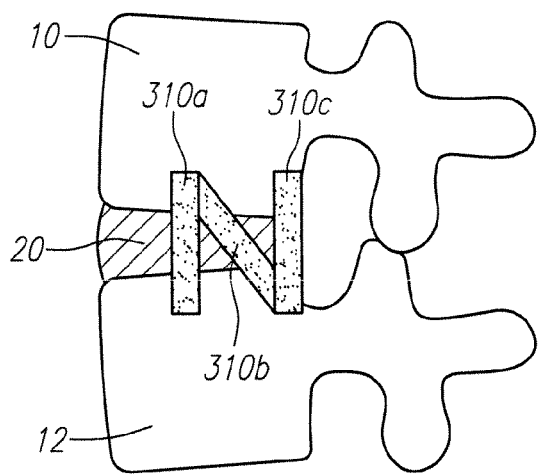
FIG. 33B is a lateral view of the embodiment in FIG. 32A showing the anti-adhesion sleeve placed over the flexible longitudinal elements.

In some embodiments, an anti-adhesion sleeve 310 t may be placed over the flexible longitudinal elements 314a-f illustrated in FIGS. 32A-B. The sleeve 310 has a first portion 311 comprising an elongate tubular member having a lumen there through that is adapted to receive a portion of the flexible longitudinal elements 314a-f there through. The sleeve 310 has a second portion 313 that extends the length of and serves to cover the flexible longitudinal element. The sleeve could be made of ePTFE material. In use, as shown in FIG. 33B, the longitudinal fixation elements 314a,b,c were treaded through the lumens 311a,b,c of sleeves 310a,b,c and attached to anchors 502a,b and 503a,b prior to insertion in the spine. After tension is applied to the fixation elements and the locking mechanisms on the anchors 502a,b were locked, as described above, the second portion 313 of the sleeves 310a,b,c is positioned to cover the portion of the fixation elements 314a,b,c extending between anchors 502a,b and 503a,b.

Figure 34:
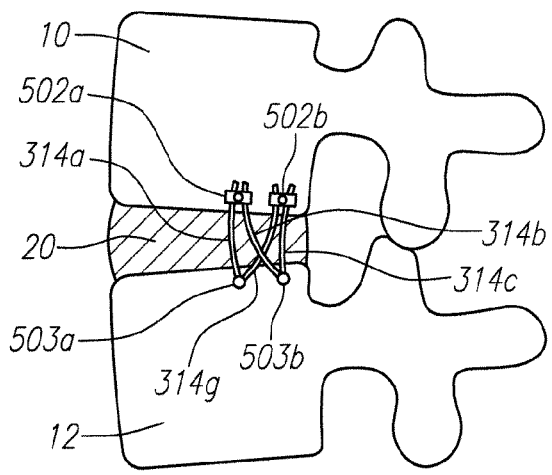
FIG. 34 is a lateral view of a portion of the spine illustrating an alternative arrangement for a flexible spinal stabilization system applied to the posterior-lateral portion of the spine.

In some embodiments, four longitudinal fixation elements can be used on each side of the posterior-lateral spine to provide additional compression to the vertebrae. For example, as shown in FIG. 34, four flexible longitudinal elements 314a,b,c,g can be threaded through locking anchors 502a,b and eyelet anchors 503a,b to provide a second diagonal fixation arm on each side of the spine. The diagonal longitudinal elements 314b,g resist axial rotation of the spine, anterior translation of the cranial vertebra 10 relative to the caudal vertebra 12, and posterior translation of the cranial vertebra 10 relative to the caudal vertebra 12.

Figure 35:
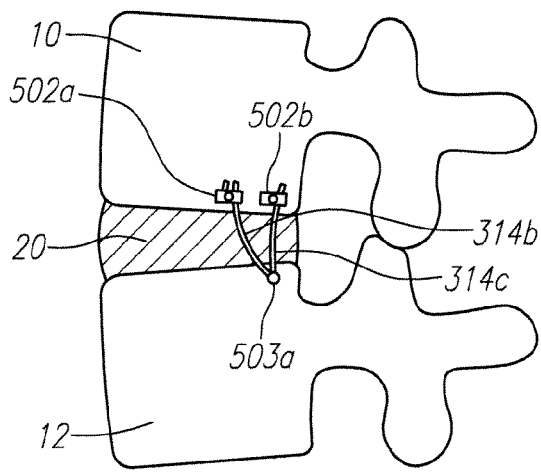
FIG. 35 is a lateral view of a portion of the spine illustrating an alternative arrangement for a flexible spinal stabilization system applied to the posterior-lateral portion of the spine.

Alternatively, in other embodiments two longitudinal fixation elements on each side of the posterior-lateral spine may provide sufficient compression across the vertebrae 10,12. For example, as shown in FIG. 35, two flexible longitudinal elements 314b,c are used on each side of the spine. Anchors 502a,b and 503a are pre-threaded with fixation elements 314b,c as previously described above and inserted into vertebrae 10,12 on the posterior lateral corners of the vertebral bodies. Tension is then applied to the ends of the fixation elements extending from anchors 502a,b. Once the desired amount of tension has been applied, the locking mechanisms of anchors 502a,b are engaged to maintain tension on the fixation elements 314b,c. The same system is then applied to the opposite side of the vertebrae as described above. Such elements resist spinal flexion and lateral bending. The diagonal longitudinal elements 314b also resist axial rotation and anterior translation of the cranial vertebra 10 relative to the caudal vertebra 12.

Figure 36A:
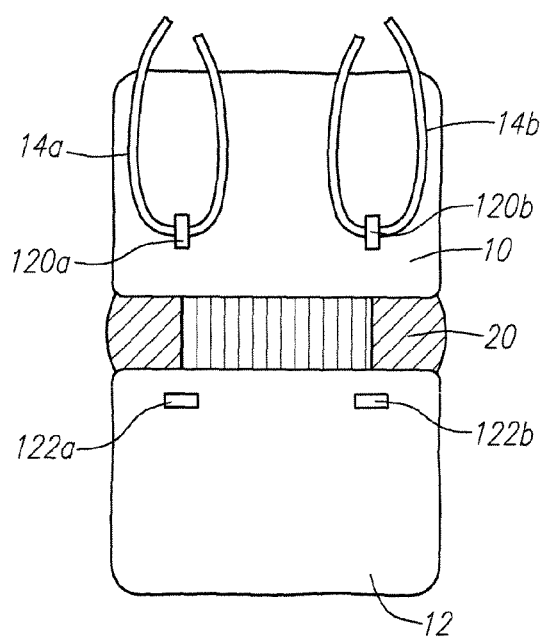
FIG. 36A is an anterior view of a portion of the spine and an alternative embodiment of flexible spinal stabilization system.
Figure 36B:
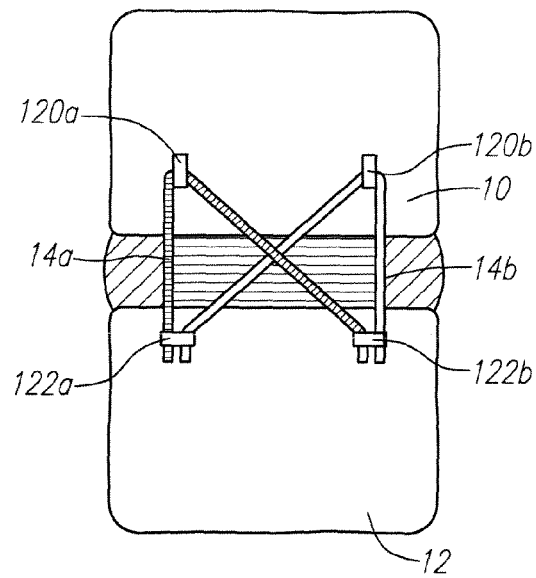
FIG. 36B is an anterior view of the embodiment in FIG. 36A showing the flexible longitudinal elements fastened to the caudal anchors.

FIG. 36A-36B illustrate an alternative method for applying a flexible stabilization device to vertebrae 10,12. Anchors 120a,b pre-threaded with flexible longitudinal elements 14a,b were placed into the cranial vertebra 10. The flexible longitudinal elements 14a,b are preferably fastened to the anchors 120a,b such that the flexible longitudinal element 14a,b can not slide through the anchors 120a,b. For example, the anchors 120a,b can be crimped around the flexible longitudinal element 14q,b after the flexible element is passed through a hole in the anchors 12a.b. Such configuration enables application of tension to one end of the flexible longitudinal element 14 without applying tension to the second end of the flexible element 14. An intradiscal device such as an interbody fusion cage 20 or total disc replacement (TDR) was placed between the vertebrae. Two anchors 122a,b with a mechanism to fasten the flexible longitudinal fixation elements were inserted into the vertebra caudal to the disc 12. Anchors 122a,b can comprise cam locking anchors as illustrated in FIGS. 1A-C, screw locking anchors as illustrated in FIGS. 8A-B or any other anchors with a suitable locking mechanism. However, in this embodiment, the locking mechanism will be threaded after the anchors have been inserted. An in growth component (not shown) such as polyester mesh and/or an anti-adhesion component such as a sheet of ePTFE is preferably placed under and over the flexible longitudinal fixation members as described in FIGS. 21B-21F and FIGS. 28F-29E.

As shown in FIG. 36B, the ends of the flexible longitudinal elements 14a,b are then threaded through the fastening mechanism(s) in the anchors 122a,b in the caudal vertebra 12. The first end of the flexible longitudinal element 14a is inserted into a first anchor 122a and the second end of the flexible longitudinal element 14a is inserted into the second anchor 122b. The first end of the flexible longitudinal element 14b is inserted into a anchor 122b and the second end of the flexible longitudinal element 14b is inserted into anchor 122a to form a cross-braced arrangement joining vertebrae 10,12. The fastening mechanism(s) of the anchors 122a,b in the caudal vertebra preferably maintain tension on the flexible elements 14 as the flexible elements 14a,b are repeatedly tightened (by repeatedly applying tension to the ends of the flexible elements). For example, in one embodiment, the Opus suture anchor (ArthroCare, Austin Tex.) could be used to repeatedly apply tension to the flexible longitudinal elements.

In some embodiments, a device that moves the spine and a TDR could be used to help surgeons determine the proper amount of tension to apply to the flexible longitudinal elements when such system is used with TDRs. For example, pins with spherical heads could be placed into the anterior surface of the vertebrae. A length adjustable tool with spherical concavities could be applied over the heads of the pins. Lengthening the adjustable tool causes spinal extension. The preferred amount of spinal extension could be measured by intra-operative x-ray or by the amount of force applied to the tool. For example, surgeons may prefer to place the spine into 5 degrees of extension, as determined by intra-operative x-ray, or place the spine into the amount of extension caused by application of a 200 Newton distraction force. A 40 Newton tension force could be applied to the flexible elements before final tightening of the anchor locking mechanism, with the spine in the extended position. This enables the flexible longitudinal elements to act as check reins to prevent excessive spinal extension following TDR insertion. Alternative amounts of spinal motion in alternative directions, such as spinal flexion, lateral bending, or axial rotation, or alternative amounts of force, such as about 40, about 50, about 70, about 100, about 300, or about 400 N could be used in the invention.

Figure 37A:
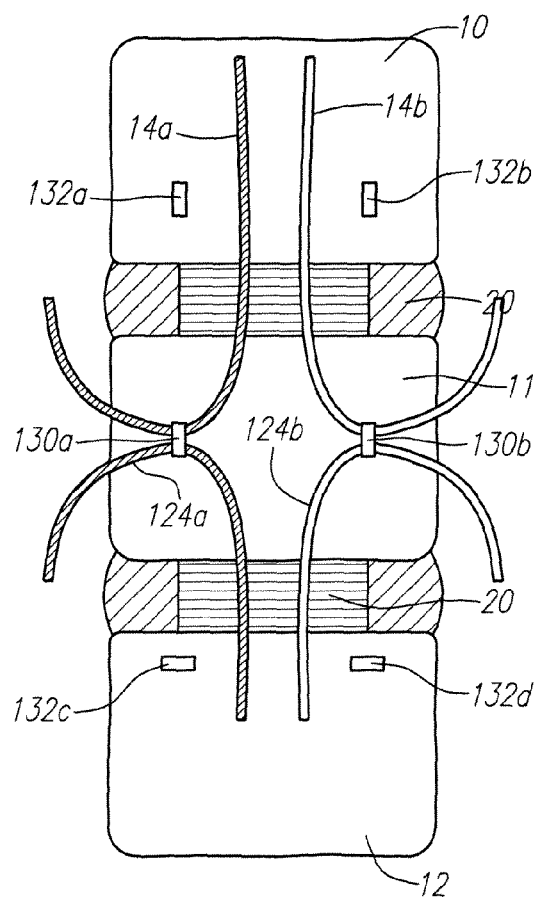
FIG. 37A is an anterior view of a portion of the spine and an alternative embodiment of flexible spinal stabilization system for two-levels.
Figure 37B:
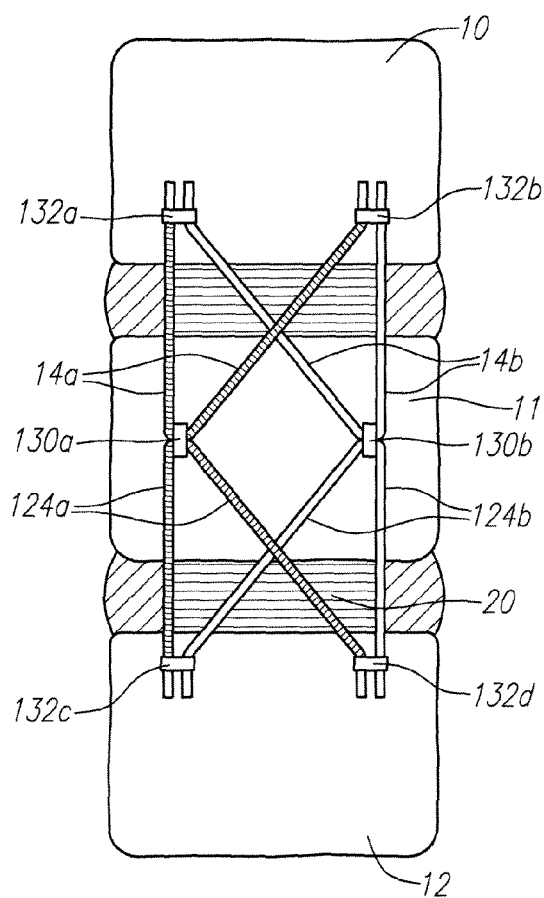
FIG. 37B is an anterior view of the embodiment in FIG. 37A showing the flexible longitudinal elements fastened to the cranial and caudal anchors

In some embodiments, as shown in FIGS. 37A-B the flexible stabilization system described in FIGS. 36A-B can be used to stabilize multiple vertebral levels. Here, anchors 130a,b with two flexible longitudinal elements 14 and 124 per anchor were placed into the intermediate vertebra 11. Anchors 132a-d with a fastening mechanism as described above were placed into the cranial 10 and the caudal 12 vertebra. Intradiscal devices 20 were placed into the discs between the vertebrae 10, 11, 12. The flexible fixation elements 14a,b and 124a,b were threaded through anchors 130a,b prior to insertion and were fixed in place such that the flexible longitudinal elements 14a,b and 124a,b can not slide through the anchors 130a,b, enabling application of tension to one end of the flexible longitudinal elements 14a,b and 124a,b without applying tension to the second end of the flexible element 14a,b and 124a,b.

Next, as shown in FIG. 37B, the ends of the flexible longitudinal elements were fastened to the anchors in the cranial and the caudal vertebra in the configuration shown. As shown in FIG. 36B, the ends of the flexible longitudinal elements 14a,b and 124a,b are then threaded through the fastening mechanism(s) in the anchors 132a,b in the cranial vertebra 10 and anchors 132c,d in the caudal vertebra 12 to form a cross-braced arrangement joining vertebrae 10,11,12. Tension is applied to each end of the fixation elements 14ab and 124a,b after they have been threaded through the fastening mechanism(s) in anchors 132a-d and the fastening mechanisms are engaged to a maintain the desired tension. Since the fixation elements were fixed in place in anchors 130a,b, each end of the fixation element is able to be individually tensioned. For example in some embodiments, more tension can be applied to the vertical fixation members to create more resistance to spinal extension. Alternatively, more tension can be applied to the diagonal fixation members to create more resistance to axial rotation.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for stabilizing a spinal segment comprising a first and a second vertebrae, the method comprising the steps of:
    providing first and second anchors, wherein each anchor has a first portion adapted to be inserted into a vertebra and a second portion adapted to engage an elongate element;
    providing third and fourth anchors, wherein each anchor has a first portion adapted to be inserted into a vertebra and a second portion adapted to engage an elongate element;
    attaching the first and second anchors to the first vertebra;
    attaching the third and fourth anchors to the second vertebra, wherein the attachments of the first, second, third, and fourth anchors in the first and second vertebrae define an area;
    positioning a mesh component over at least a portion of the first and second vertebrae, wherein at least a portion of the mesh component lies within the area;
    connecting the first, second, and third anchors with a first elongate element; and
    connecting the first, second, and fourth anchors with a second elongate element,
    wherein the first and second elongate elements hold at least a portion of the mesh component within the area.

2. The method of claim 1, wherein the second portion of each of the first and second anchors comprises a hook adapted to engage one of the first or second elongate elements, wherein one of the first or second elongate elements is connected to the second portion of one of the first or second anchors by looping the first or second elongate element around the hook.

3. The method of claim 1, wherein the second portion of each of the third and fourth anchors comprises a cam that is adapted to frictionally engage one of the first or second elongate elements upon rotation of the cam, wherein one of the first or second elongate elements is connected to the second portion of one of the third or fourth anchors by frictionally engaging one of the first or second elongate elements by rotating the cam.

4. The method of claim 1, wherein the second portion of each of the third and fourth anchors comprises an enlarged end having a generally oblong member, a pair of generally arcuate sleeves, and an annulus disposed therebetween, the annulus adapted to receive a first and a second end region of one of the first or second elongate elements there through, the annulus extending along an axis perpendicular to a longitudinal axis of the first portion of each of the third and fourth anchors.

5. The method of claim 4, wherein one of the first or second elongate elements is connected to the second portion of one of the third or fourth anchors by passing the first and second end regions of one of the first or second elongate elements through the annulus.

6. The method of claim 1, wherein the second portion of each of the third and fourth anchors comprises an enlarged end having a first passage adapted to slidably receive a first end region of the first or second elongate element, the passage extending along an axis perpendicular to a longitudinal axis of the first portion of each of the third and fourth anchors, wherein at least one of the first or second elongate elements is connected to the second portion of one of the third and fourth anchors by inserting the first end region of the first or second elongate element through the first passage of the third or fourth elongate anchors.

7. The method of claim 6, wherein a second end region of the first or second elongate elements is connected to the enlarged end of the third or fourth anchors.

8. The method of claim 7, wherein the second end region of the first or second elongate elements is connected to the enlarged end of the third or fourth anchors with a clamp.

9. The method of claim 1, further comprising the step of applying tension to at least one of the first and second elongate elements.

10. The method of claim 9, wherein tension is applied by pulling on an end region of at least one of the first or second elongate element.

11. The method of claim 10, wherein tension is applied by inserting the end region of the first or second elongate element into a passage through an elongate member and rotating the elongate member such that the first or second elongate element is wrapped around an outer surface of the elongate member.

12. The method of claim 11, further comprising the step of cutting off at least a portion of the end region of the first or second elongate element.

13. The method of claim 6, wherein the second portion of each of the third and fourth anchors further comprises a first threaded bore extending along an axis substantially parallel to a longitudinal axis of the first portion of each of the third and fourth anchors, wherein the first threaded bore communicates with the first passage.

14. The method of claim 13, further comprising the steps of:
inserting a first screw into the first threaded bore in the third anchor; and
inserting a second screw into the first threaded bore in the fourth anchor,
wherein the first and second screws are inserted to extend into the first passages of the third and fourth anchors, respectively, and wherein the first and second screws are each inserted into one of the first or second elongate elements lying within the first passages.

15. The method of claim 6, wherein the second portion of each of the third and fourth anchors further comprises a second passage adapted to slidably receive a second end region of the first or second elongate element, the second passage extending along an axis perpendicular to a longitudinal axis of the first portion of each of the third and fourth anchors,
wherein at least one of the first or second elongate elements is connected to the second portion of one of the third and fourth anchors by inserting the second end region of the first or second elongate element through the second passage of the third or fourth elongate anchors.

16. The method of claim 15, wherein one of the first or second elongate elements is connected to the second portion of the third anchor by inserting the first end region through the first passage and the second end region through the second passage.

17. The method of claim 15, wherein one of the first or second elongate elements is connected to the second portion of the fourth anchor by inserting the first end region through the first passage and the second end region through the second passage.

18. The method of claim 15, wherein the second portion of each of the third and fourth anchors further comprises third and fourth passages, each or which are adapted to slidably receive one of the first or second end regions of the first or second elongate elements, the third and fourth passages extending along axes perpendicular to a longitudinal axis of the first portion of each of the third and fourth anchors.

19. The method of claim 18, wherein one of the first or second elongate elements is connected to the second portion of the third anchor by inserting the each of the first and second end regions through at least two of the first, second, third, and fourth passages.

20. The method of claim 18, wherein one of the first or second elongate elements is connected to the second portion of the fourth anchor by inserting the each of the first and second end regions through at least two of the first, second, third, and fourth passages.

21. The method of claim 1, further comprising the step of positioning an anti-adhesion cover over at least a portion of the area, wherein at least one of the first and second anchors and at least one of the third and fourth anchors are not covered by the anti-adhesion cover.

22. The method of claim 1, wherein each of the first portion of each of the first, second, third, and fourth anchors comprises a cavity that extends through at least part of the first portion of each of the first, second, third, and fourth anchors.

23. The method of claim 22, wherein the second portions of the first, second, third, and fourth anchors each comprise first, second, third, and fourth detachable components, respectively, each comprising an enlarged end having at least one passage adapted to slidably receive at least one of the first and second elongate elements and extending along an axis perpendicular to a longitudinal axis of the first portion of each of the first, second, third, and fourth anchors, and a deformable element sized for insertion into the cavity and adapted to bear against a portion of the cavity.

24. The method of claim 23, wherein the first and second elongate elements are slidably disposed within the at least one passage of the detachable component, and wherein the first and second elongate elements are connected to the first and second anchors by inserting the deformable element of the first and second detachable components into the cavities of the first and second anchors, respectively.

25. The method of claim 23, wherein the first and second end regions of the first elongate element are slidably disposed within the at least one passage of one of the third or fourth detachable components, and wherein the first elongate element is connected to one of the third and fourth anchors by inserting the deformable element of one of the third and fourth detachable components into the cavities of one of the third and fourth anchors.

26. The method of claim 23, wherein the first and second end regions of the second elongate element are slidably disposed within the at least one passage of one of the third or fourth detachable components, and wherein the second elongate element is connected to one of the third and fourth anchors by inserting the deformable element of one of the third and fourth detachable components into the cavities of one of the third and fourth anchors.

* * * * *